United States Patent
Okada et al.

(10) Patent No.: US 9,243,098 B2
(45) Date of Patent: Jan. 26, 2016

(54) COMPOUND, POLYMER, CROSS-LINKED COMPOUND OF POLYMER, AND OPTICAL ELEMENT INCLUDING CROSS-LINKED COMPOUND

(75) Inventors: Seiji Okada, Pittsburgh (JP); Ryo Ogawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/235,437

(22) PCT Filed: Jul. 25, 2012

(86) PCT No.: PCT/JP2012/069533
§ 371 (c)(1),
(2), (4) Date: Jan. 27, 2014

(87) PCT Pub. No.: WO2013/018817
PCT Pub. Date: Feb. 7, 2013

(65) Prior Publication Data
US 2014/0163175 A1 Jun. 12, 2014

(30) Foreign Application Priority Data
Jul. 29, 2011 (JP) .................................. 2011-166969

(51) Int. Cl.
*C07C 13/06* (2006.01)
*C08F 232/08* (2006.01)
(Continued)

(52) U.S. Cl.
CPC .............. *C08F 232/08* (2013.01); *C07C 13/06* (2013.01); *C07C 13/42* (2013.01); *C07C 13/44* (2013.01); *C07D 209/52* (2013.01); *C07D 209/96* (2013.01); *C08F 32/08* (2013.01); *C08F 132/08* (2013.01); *C08G 61/08* (2013.01); *G02B 1/04* (2013.01); *C07C 2102/06* (2013.01); *C07C 2102/42* (2013.01); *C08F 2500/25* (2013.01); *C08F 2810/20* (2013.01); *C08G 2261/135* (2013.01); *C08G 2261/148* (2013.01); *C08G2261/3324* (2013.01); *C08G 2261/418* (2013.01); *C08G 2261/76* (2013.01)

(58) Field of Classification Search
None
See application file for complete search history.

(56) References Cited

U.S. PATENT DOCUMENTS

| 4,724,260 | A * | 2/1988 | Kirchhoff et al. ............. 546/112 |
| 2006/0246681 | A1* | 11/2006 | Li et al. ......................... 438/421 |
| 2009/0124773 | A1* | 5/2009 | Zhou et al. .................... 526/209 |

FOREIGN PATENT DOCUMENTS

| JP | 2006-172822 A | 6/2006 |
| JP | 2007-314668 A | 12/2007 |

(Continued)

OTHER PUBLICATIONS

Watabe, Chemistry Letters, pp. 1791-1974, vol. 13, No. 10, 2006.*

*Primary Examiner* — Robert C Boyle
(74) *Attorney, Agent, or Firm* — Canon USA Inc. IP Division

(57) ABSTRACT

Conventional cross-linked cyclic olefin polymers do not have a sufficiently low linear expansion coefficient. A compound having a structure represented by the following formula (a).

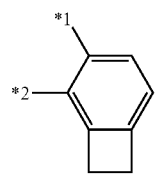

8 Claims, 4 Drawing Sheets

(51) Int. Cl.
*C08F 32/08* (2006.01)
*C07D 209/52* (2006.01)
*C07C 13/42* (2006.01)
*G02B 1/04* (2006.01)
*C07C 13/44* (2006.01)
*C08G 61/08* (2006.01)
*C07D 209/96* (2006.01)
*C08F 132/08* (2006.01)

(56) References Cited

FOREIGN PATENT DOCUMENTS

| | | |
|---|---|---|
| JP | 2011-503290 A | 1/2011 |
| JP | 2011-074293 A | 4/2011 |
| WO | 2004/073018 A | 8/2004 |

* cited by examiner

COMPOUND, POLYMER, CROSS-LINKED COMPOUND OF POLYMER, AND OPTICAL ELEMENT INCLUDING CROSS-LINKED COMPOUND

TECHNICAL FIELD

The present invention relates to a novel compound, a polymer, a cross-linked compound of the polymer, and an optical element including the cross-linked compound.

BACKGROUND ART

Although cyclic olefin polymers have high transparency and are useful as materials for optical elements, such as lenses, it is known that cyclic olefin polymers have high linear expansion coefficients.

It is known that a technique for cross-linking a cyclic olefin polymer produces a material having a low linear expansion coefficient. PTL 1 discloses the cross-link of a cross-linkable cyclic olefin polymer having the following formula (1).

[Chem. 1]

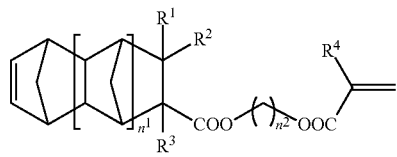
(1)

In the formula (1), $n^1$ denotes 1 or 2, $n^2$ denotes an integer of 1 or more and 12 or less, $R^1$, $R^2$, and $R^3$ independently denote a hydrogen atom or a hydrocarbon group having 1 or more and 10 or less carbon atoms, and $R^4$ denotes a hydrogen atom or a methyl group.

However, the cyclic olefin polymer having the formula (1) disclosed in PTL 1 has a low glass transition temperature and a slightly high linear expansion coefficient.

CITATION LIST

Patent Literature

PTL 1 Japanese Patent Laid-Open No. 2011-74293 (Paragraph [0008])

SUMMARY OF INVENTION

A compound according to an embodiment of the present invention has the following general formula (I):

A-Z—Bφ  (I)

wherein A has the following formula (a), Bφ has the following formula (b1) or (b2), and Z denotes a direct bond (z1) or has one of the formulae (z2) to (z12),

[Chem. 2]

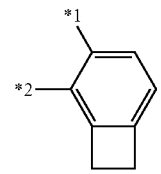
(a)

In the formula (a), *1 and *2 denote a bonding arm, one of *1 and *2 is bonded to Z of the formula (I), and the other of *1 and *2 not bonded to Z of the formula (I) is bonded to a hydrogen atom.

[Chem. 3]

(b1)

(b2)

In the formulae (b1) and (b2), * denotes a bonding arm and is bonded to Z of the formula (I).

[Chem. 4]

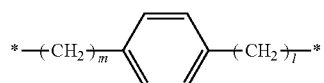
(z2)

(z3)

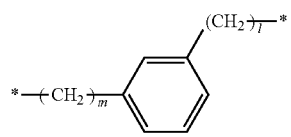
(z4)

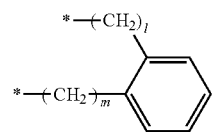
(z5)

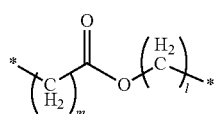
(z6)

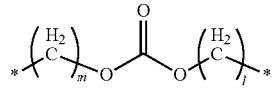
(z7)

In each of the formulae (z2) to (z12), two *'s denote a bonding arm and are bonded to A or Bφ of the formula (I), and n, m, and l independently denote an integer of 0 to 5.

A compound according to another embodiment of the present invention has the following general formula (II):

Cφ-Y-D                               (II)

wherein Cφ has the following formula (c), D has one of the following formulae, (d1) and (d2), and Y is a direct bond (y1) or has one of the formulae (y2) to (y12).

[Chem. 5]

In the formula (c), *3 and *4 denote a bonding arm, one of *3 and *4 is bonded to Y of the formula (II), and the other of *3 and *4 not bonded to Y of the formula (II) is bonded to a hydrogen atom.

[Chem. 6]

In the formulae (d1) and (d2), * denotes a bonding arm and is bonded to Y of the formula (II).

[Chem. 7]

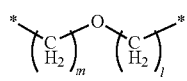 (y12)

In each of the formulae (y2) to (y12), two *'s denote a bonding arm and are bonded to Cφ or D of the formula (II), and n, m, and l independently denote an integer of 0 to 5.

A polymer according to an embodiment of the present invention has a constitutional repeating unit represented by one of the formulae (e1) to (e3).

[Chem. 8]

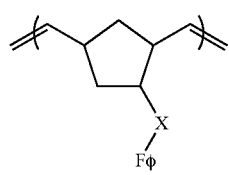 (e1)

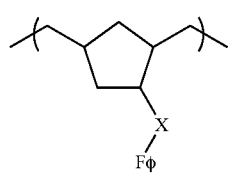 (e2)

 (e3)

In the formulae (e1) to (e3), Fφ has the following formula (f), and X is a direct bond (x1) or has one of the formulae (x2) to (x12).

[Chem. 9]

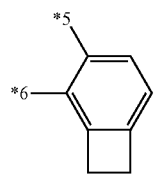 (f)

In the formula (f), *5 and *6 denote a bonding arm, one of *5 and *6 is bonded to X of the formulae (e1) to (e3), and the other of *5 and *6 not bonded to X of the formulae (e1) to (e3) is bonded to a hydrogen atom.

[Chem. 10]

 (x2)

 (x3)

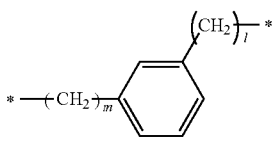 (x4)

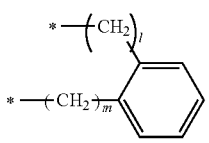 (x5)

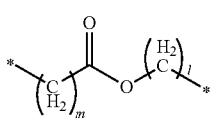 (x6)

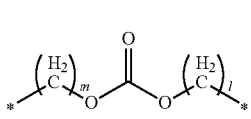 (x7)

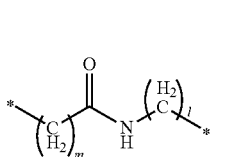 (x8)

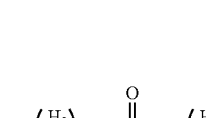 (x9)

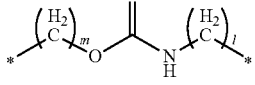 (x10)

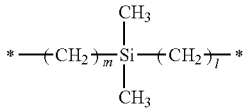 (x11)

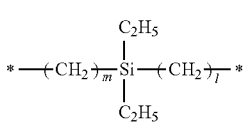 (x12)

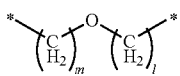

In each of the formulae (x2) to (x12), two *'s denote a bonding arm and are bonded to a carbon atom of an alicyclic structure or Fφ of the formulae, (e1) to (e3), and n, m, and l independently denote an integer of 0 to 5.

A polymer according to still another embodiment of the present invention has a constitutional repeating unit represented by one of the formulae (g1) to (g3).

[Chem. 11]

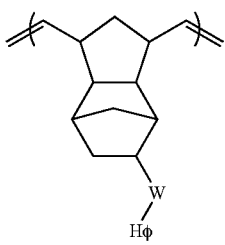
(g1)

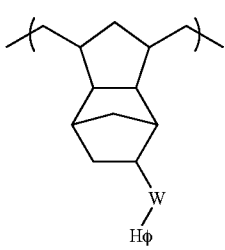
(g2)

(g3)

In the formulae (g1) to (g3), Hφ has the following formula (h), and W is a direct bond (w1) or has one of the formulae (w2) to (w12).

[Chem. 12]

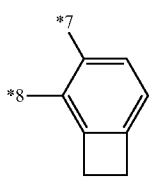
(h)

In the formula (h), *7 and *8 denote a bonding arm, one of *7 and *8 is bonded to W of the formulae (g1) to (g3), and the other of *7 and *8 not bonded to W of the formulae (g1) to (g3) is bonded to a hydrogen atom.

[Chem. 13]

$*\!-\!(CH_2)_n\!-\!*$ (w2)

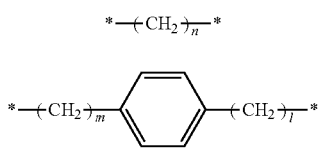
(w3)

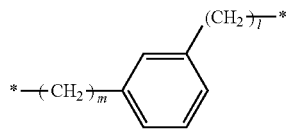
(w4)

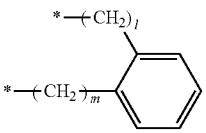
(w5)

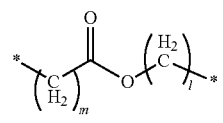
(w6)

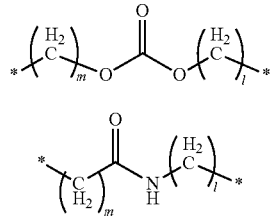
(w7)

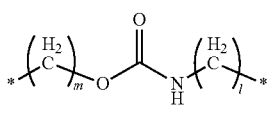
(w8)

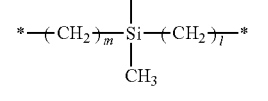
(w9)

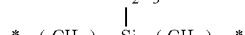
(w10)

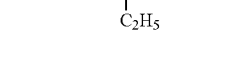
(w11)

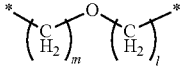
(w12)

In each of the formulae (w2) to (w12), two *'s denote a bonding arm and are bonded to a carbon atom of an alicyclic structure or H of the formulae (g1) to (g3), and n, m, and l independently denote an integer of 0 to 5.

A polymer according to still another embodiment of the present invention has a constitutional repeating unit represented by one of the formulae (i1) to (i3).

[Chem. 14]

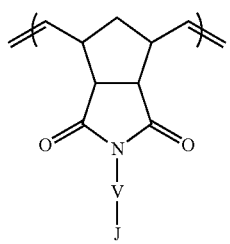
(i1)

-continued

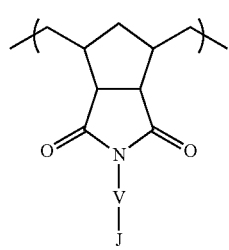
(i2)

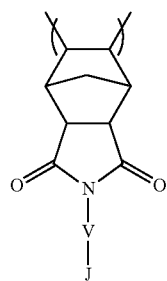
(i3)

In the formulae (i1) to (i3), J has the following formula (j), and V is a direct bond (v1) or has one of the formulae (v2) to (v12).

[Chem. 15]

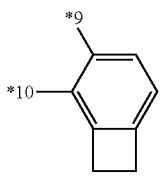
(j)

In the formula (j), *9 and *10 denote a bonding arm, one of *9 and *10 is bonded to V of the formulae (i1) to (i3), and the other of *9 and *10 not bonded to V of the formulae (i1) to (i3) is bonded to a hydrogen atom.

[Chem. 16]

(v2)

(v3)

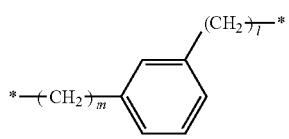
(v4)

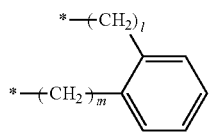
(v5)

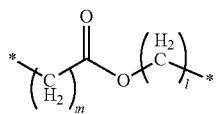
(v6)

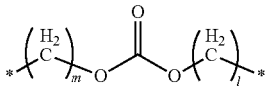
(v7)

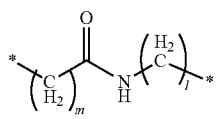
(v8)

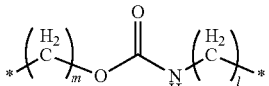
(v9)

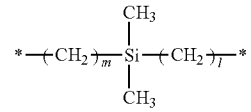
(v10)

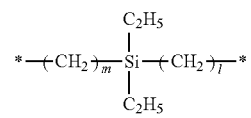
(v11)

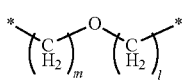
(v12)

In each of the formulae (v2) to (v12), two *'s denote a bonding arm and are bonded to a nitrogen atom or J of the formulae (i1) to (i3), and n, m, and l independently denote an integer of 0 to 5.

A polymer according to still another embodiment of the present invention has a constitutional repeating unit represented by one of the formulae (k1) to (k3).

[Chem. 17]

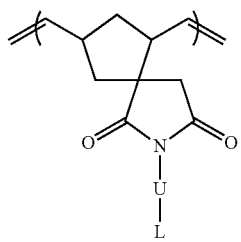
(k1)

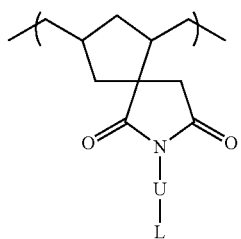
(k2)

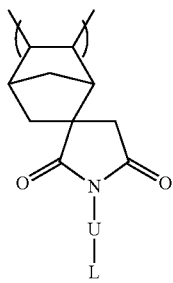
(k3)

In the formulae (k1) to (k3), L has the following formula (l), and U is a direct bond (u1) or has one of the formulae (u2) to (u12).

[Chem. 18]

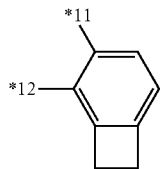
(l)

In the formula (l), *11 and *12 denote a bonding arm, one of *11 and *12 is bonded to U of the formulae (k1) to (k3), and the other of *11 and *12 not bonded to U of the formulae (k1) to (k3) is bonded to a hydrogen atom.

[Chem. 19]

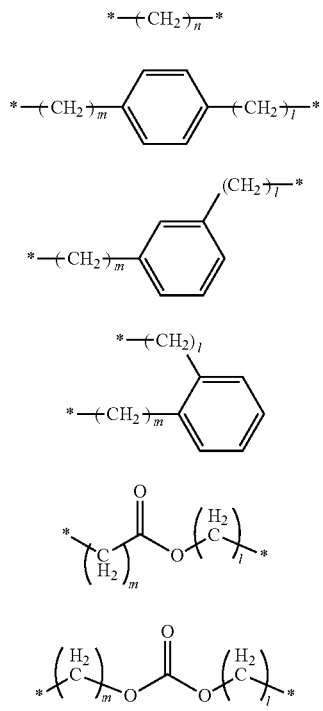

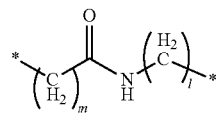
(u8)

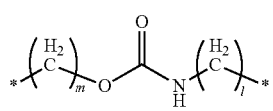
(u9)

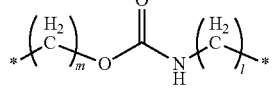
(u10)

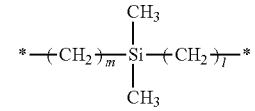
(u11)

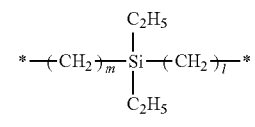
(u12)

In each of the formulae (u2) to (u12), two *'s denote a bonding arm and are bonded to a nitrogen atom or L of the formulae (k1) to (k3), and n, m, and l independently denote an integer of 0 to 5.

A cross-linked compound according to an embodiment of the present invention has the general formula (III).

M-R-T-R'-M'  (III)

In the formula (III), M and M' are polymers having a constitutional repeating unit represented by one of the formulae (m1) to (m12), each of R and R' is a direct bond (r1) or has one of the formulae (r2) to (r12), and T has the formula (t).

[Chem. 20]

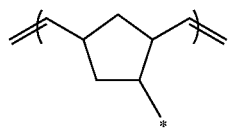
(m1)

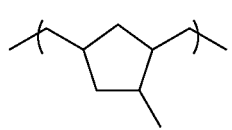
(m2)

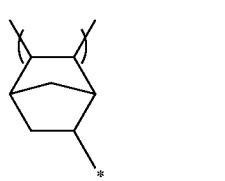
(m3)

-continued
(m4) 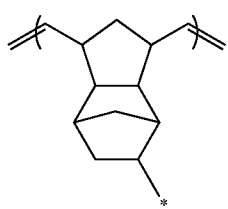
(m5) 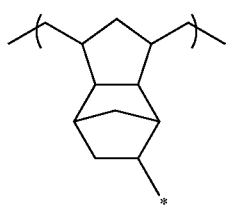
(m6) 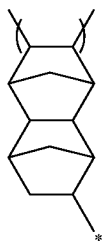
(m7) 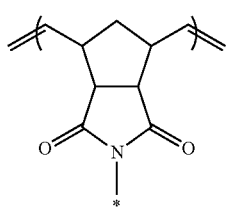
(m8) 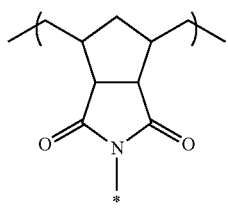
(m9) 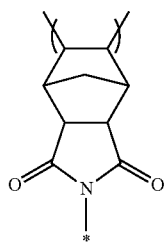
(m10) 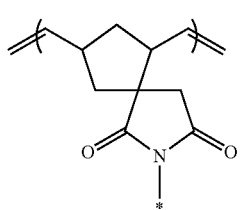
-continued
(m11) 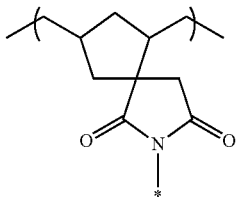
(m12) 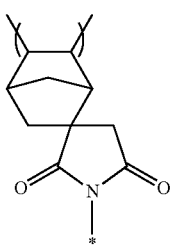
In the formulae (m1) to (m12), * denotes a bonding arm and is bonded to R or R' of the formula (III).
[Chem. 21]
(r2) 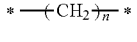
(r3) 
(r4) 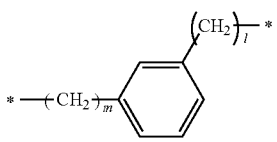
(r5) 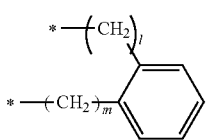
(r6) 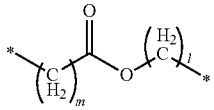
(r7) 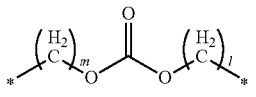
(r8) 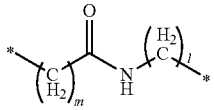
(r9) 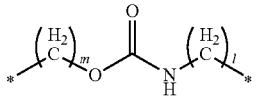

-continued

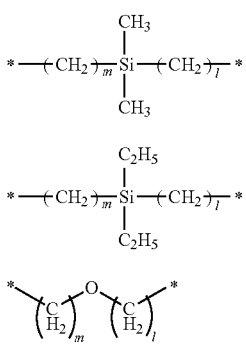

(r10)

(r11)

(r12)

In each of the formulae (r2) to (r12), two *'s denote a bonding arm and are bonded to M or M' or T of the formula (III), and n, m, and l independently denote an integer of 0 to 5.

[Chem. 22]

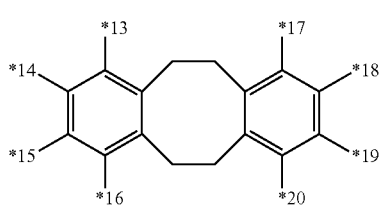

(t)

In the formula (t), *13 to *20 denote a bonding arm, one of *13 to *16 and one of *17 to *20 are bonded to M and M' of the formula (III), and the remainder of *13 to *20 not bonded to M or M' of the formula (III) are bonded to a hydrogen atom.

DESCRIPTION OF EMBODIMENTS

Figure 1:
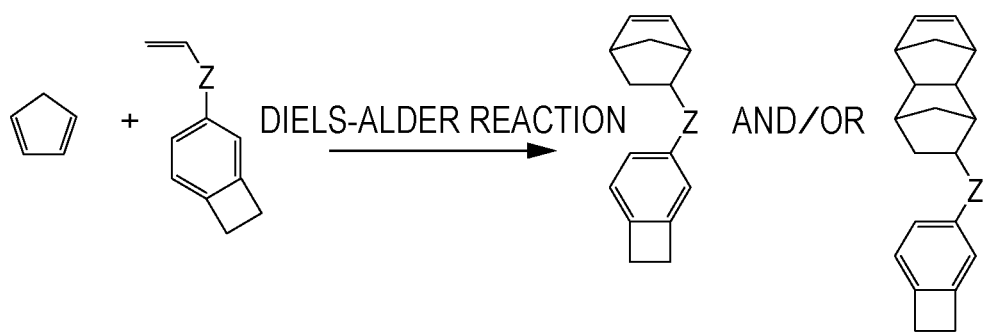
FIG. 1 is a reaction scheme in a method for producing a compound according to an embodiment of the present invention.

Embodiments of the present invention will be described below.

In the present specification, unless otherwise specified, C denotes a carbon atom, N denotes a nitrogen atom, H denotes a hydrogen atom, O denotes an oxygen atom, S denotes a sulfur atom, and Si denotes a silicon atom.

First Embodiment

Compounds

A compound according to an embodiment of the present invention has the following general formula (I):

A-Z—Bφ     (I)

wherein A has the following formula (a), Bφ has the following formula (b1) or (b2), and Z denotes a direct bond (z1) or has one of the formulae (z2) to (z12).

[Chem. 23]

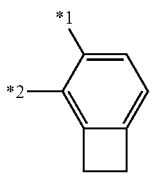

(a)

In the formula (a), *1 and *2 denote a bonding arm of a carbon atom of a phenyl ring in the formula (a), one of *1 and *2 is bonded to Z of the formula (I), and the other of *1 and *2 not bonded to Z of the formula (I) is bonded to a hydrogen atom.

[Chem. 24]

(b1)

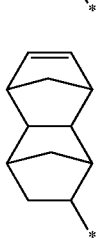

(b2)

In the formulae (b1) and (b2), * denotes a bonding arm and is bonded to Z of the formula (I).

[Chem. 25]

*—(CH$_2$)$_n$—*     (z2)

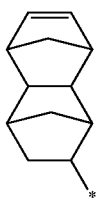

(z3)

(z4)

(z5)

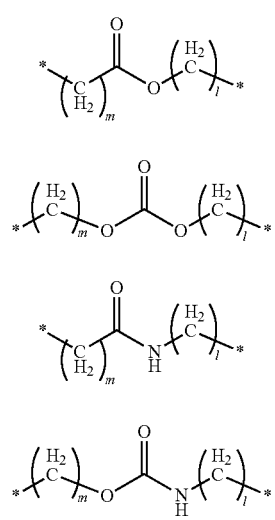

(z6)

(z7)

(z8)

(z9)

(z10)

(z11)

(z12)

In each of the formulae (z2) to (z12), two *'s denote a bonding arm and are bonded to A or Bφ of the formula (I), and n, m, and l independently denote an integer of 0 to 5.

A compound according to another embodiment of the present invention has the following general formula (II):

Cφ-Y-D     (II)

In the formula (II) Cφ has the following formula (c), D has one of the following formulae (d1) and (d2), and Y is a direct bond (y1) or has one of the formulae (y2) to (y12).

[Chem. 26]

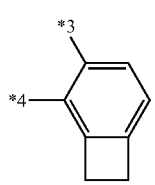

(c)

In the formula (c), *3 and *4 denote a bonding arm of a carbon atom of a phenyl ring in the formula (c), one of *3 and *4 is bonded to Y of the formula (II), and the other of *3 and *4 not bonded to Y of the formula (II) is bonded to a hydrogen atom.

[Chem. 27]

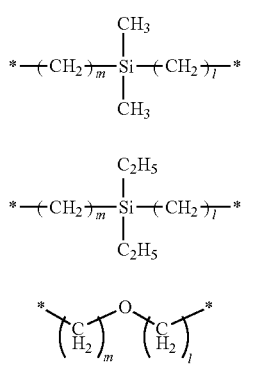

(d1)

(d2)

In the formulae (d1) and (d2), * denotes a bonding arm and is bonded to Y of the formula (II).

[Chem. 28]

$* \!-\!(CH_2)_n\!-\! *$     (y2)

(y3)

(y4)

(y5)

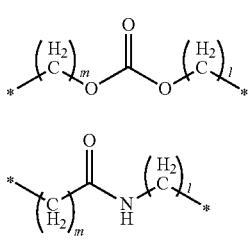

(y6)

(y7)

(y8)

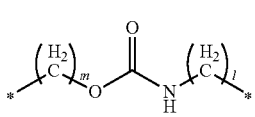

(y9)

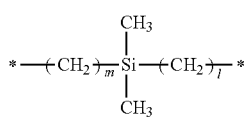 (y10)

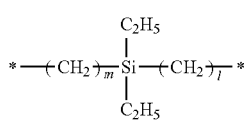 (y11)

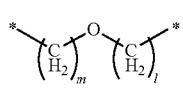 (y12)

In each of the formulae (y2) to (y12), two denote a bonding arm and are bonded to Cφ or D of the formula (II), and n, m, and independently denote an integer of 0 to 5.

A compound according to the present embodiment has one of the formulae (b1), (b2), (d1), and (d2) and can be polymerized to produce a polymer described below. The polymer can be heated to produce a cross-linked compound. The cross-linked compound has a sufficiently low linear expansion coefficient of 60 ppm/° C. or less. Because of its small dimensional change with temperature, the cross-linked compound can be suitably used as a material for optical elements and electric circuit boards.

Furthermore, the cross-linking of the polymer described below does not produce by-products, such as ethylene. Thus, the polymer can be formed into a product without air bubbles. The cross-linking of the polymer does not require a cross-linker or a cross-linking aid.

In a compound according to the present embodiment, the direct bond (z1), the moieties having the formulae (z2) to (z5), the formula (z10), the formula (z11), the direct bond (y1), the formulae (y2) to (y5), the formula (y10), and the formula (y11) have no oxygen atom, resulting in low water absorbency. The moieties having the formulae (z6) to (z12) and the formulae (y6) to (y12) have a heteroatom, resulting in good adhesion with a substrate made of a metal, such as copper, or glass.

Examples of a compound according to the present embodiment are as follows:

[Chem. 29]

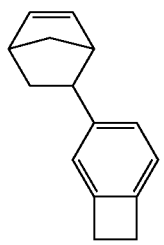 (2)

Polymer

A polymer according to an embodiment of the present invention has a constitutional repeating unit represented by one of the formulae (e1) to (e3).

[Chem. 30]

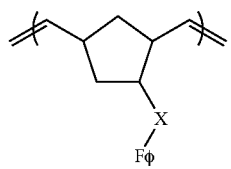 (e1)

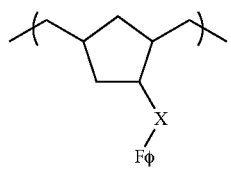 (e2)

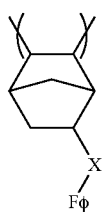 (e3)

In the formulae (e1) to (e3), Fφ has the following formula (f), and X is a direct bond (x1) or has one of the formulae (x2) to (x12).

[Chem. 31]

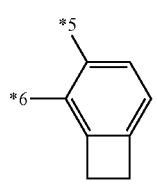 (f)

In the formula (f), *5 and *6 denote a bonding arm of a carbon atom of a phenyl ring in the formula (f), one of *5 and *6 is bonded to X of the formulae (e1) to (e3), and the other of *5 and *6 not bonded to X of the formulae (e1) to (e3) is bonded to a hydrogen atom.

[Chem. 32]

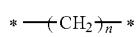 (x2)

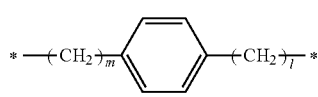 (x3)

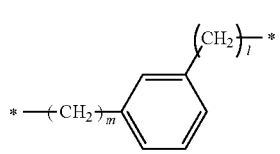 (x4)

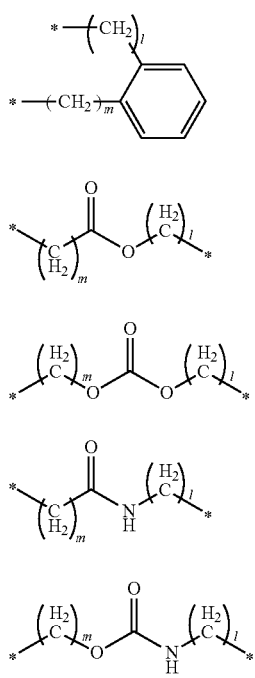

(x5)
(x6)
(x7)
(x8)
(x9)
(x10)
(x11)
(x12)

In each of the formulae (x2) to (x12), two *'s denote a bonding arm and are bonded to a carbon atom of an alicyclic structure or F of the formulae (e1) to (e3), and n, m, and l independently denote an integer of 0 to 5.

Another polymer according to the present embodiment has a constitutional repeating unit represented by one of the formulae (g1) to (g3).

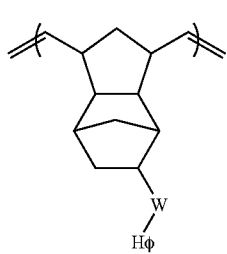

(g1)

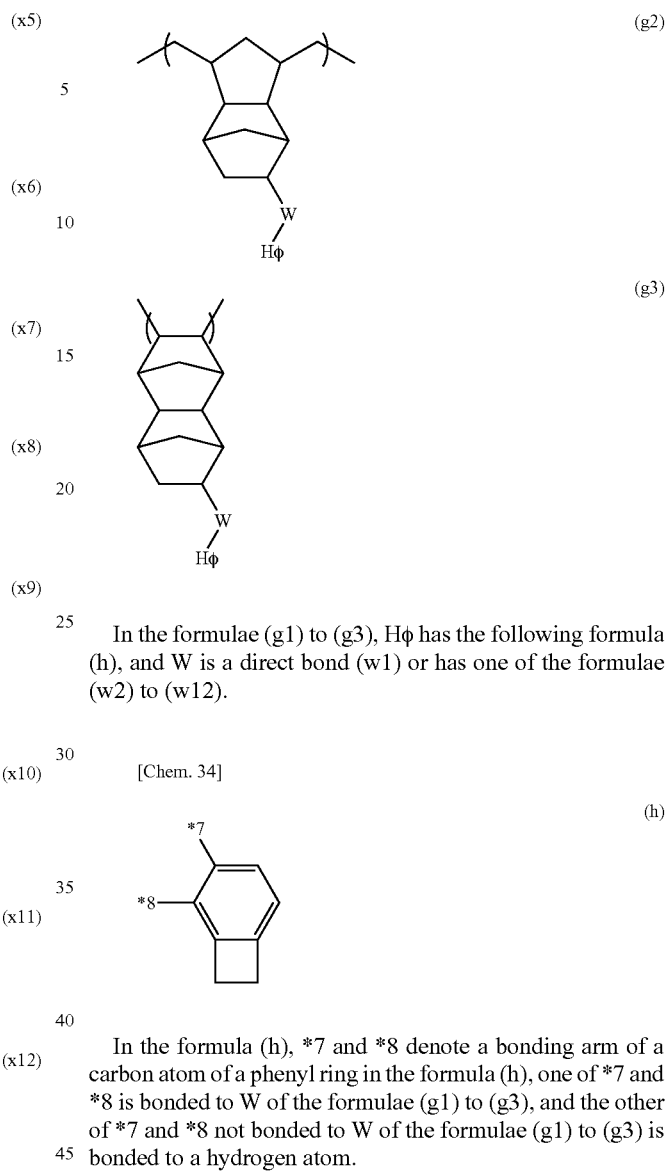

(g2)

(g3)

In the formulae (g1) to (g3), Hφ has the following formula (h), and W is a direct bond (w1) or has one of the formulae (w2) to (w12).

[Chem. 34]

(h)

In the formula (h), *7 and *8 denote a bonding arm of a carbon atom of a phenyl ring in the formula (h), one of *7 and *8 is bonded to W of the formulae (g1) to (g3), and the other of *7 and *8 not bonded to W of the formulae (g1) to (g3) is bonded to a hydrogen atom.

[Chem. 35]

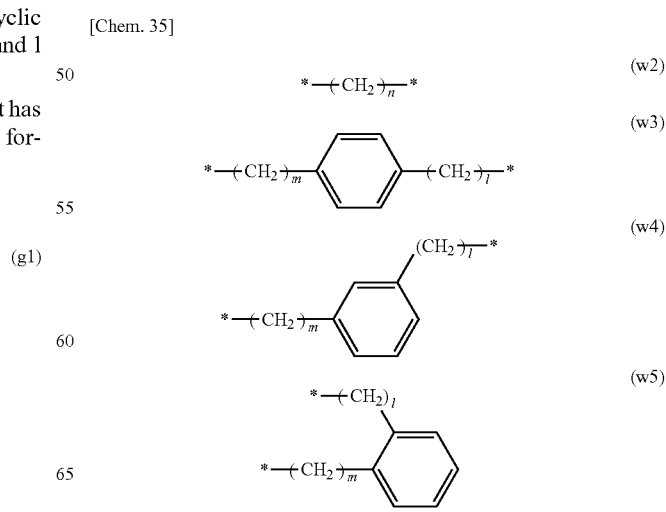

(w2)
(w3)
(w4)
(w5)

(w6) 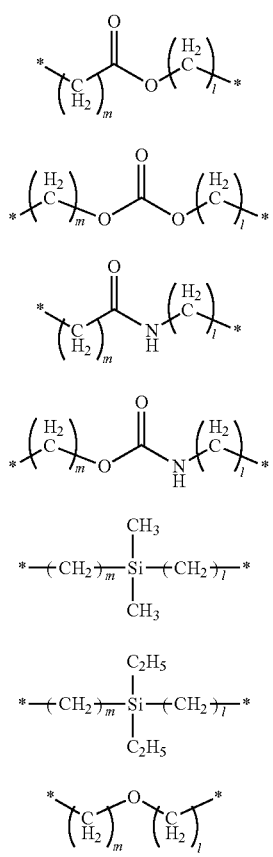

(w7)

(w8)

(w9)

(w10)

(w11)

(w12)

In each of the formulae (w2) to (w12), two *'s denote a bonding arm and are bonded to a carbon atom of an alicyclic structure or Hφ of the formulae (g1) to (g3), and n, m, and l independently denote an integer of 0 to 5.

Still another polymer according to the present embodiment has a constitutional repeating unit represented by one of the formulae (i1) to (i3).

[Chem. 36]

(i1)

(i2)

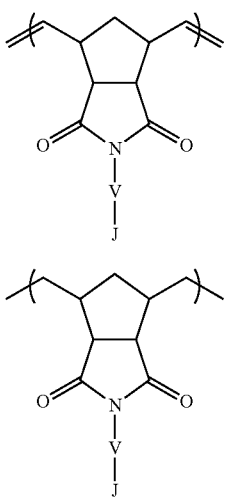

(i3)

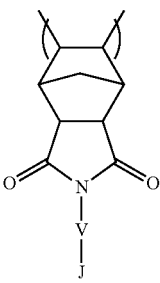

In the formulae (i1) to (i3), J has the following formula (j), and V is a direct bond (v1) or has one of the formulae (v2) to (v12).

[Chem. 37]

(j)

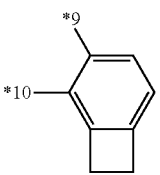

In the formula (j), *9 and *10 denote a bonding arm of a carbon atom of a phenyl ring in the formula (j), one of *9 and *10 is bonded to V of the formulae (i1) to (i3), and the other of *9 and *10 not bonded to V of the formulae (i1) to (i3) is bonded to a hydrogen atom.

[Chem. 38]

(v2) $*\!-\!(CH_2)_n\!-\!*$ (v3) 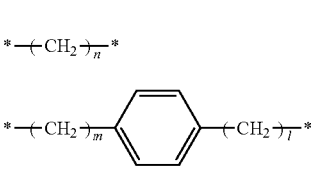

(v4) 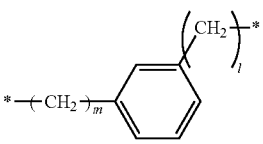

(v5) 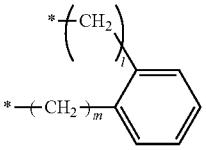

(v6) 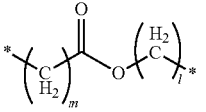

(v7) 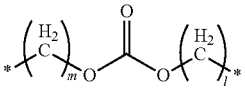

(v8) 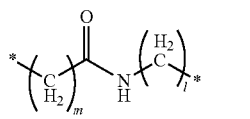

(v9) 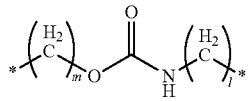

(v10) 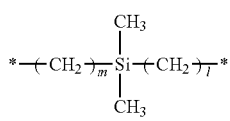

(v11) 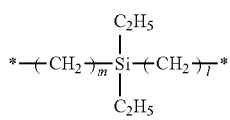

(v12) 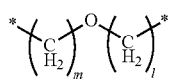

In each of the formulae (v2) to (v12), two *'s denote a bonding arm and are bonded to a nitrogen atom or J of the formulae (i1) to (i3), and n, m, and l independently denote an integer of 0 to 5.

Still another polymer according to the present embodiment has a constitutional repeating unit represented by one of the formulae (k1) to (k3).

[Chem. 39]

(k1) 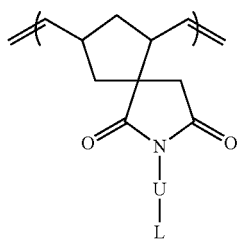

(k2) 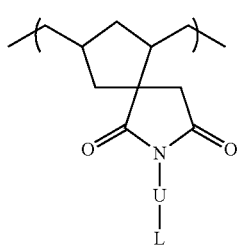

(k3) 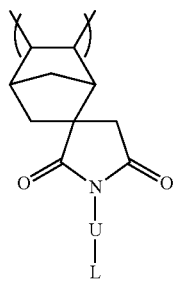

In the formulae (k1) to (k3), L has the following formula (l), and U is a direct bond (u1) or has one of the formulae (u2) to (u12).

[Chem. 40]

(l) 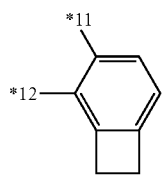

In the formula (l), *11 and *12 denote a bonding arm of a carbon atom of a phenyl ring in the formula (l), one of *11 and *12 is bonded to U of the formulae (k1) to (k3), and the other of *11 and *12 not bonded to U of the formulae (k1) to (k3) is bonded to a hydrogen atom.

[Chem. 41]

(u2) 

(u3) 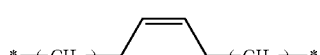

(u4) 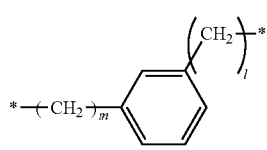

(u5) 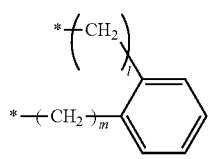

(u6) 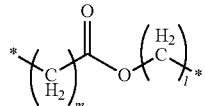

(u7) 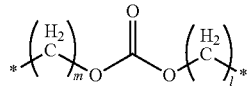

-continued (u8)
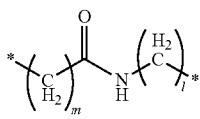

(u9)
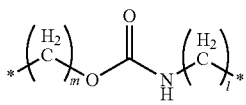

(u10)
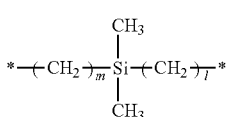

(u11)
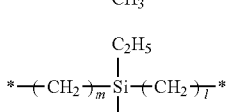

(u12)
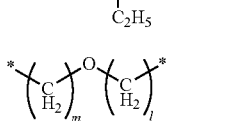

In each of the formulae (u2) to (u12), two *'s denote a bonding arm and are bonded to a nitrogen atom or L of the formulae (k1) to (k3), and n, m, and l independently denote an integer of 0 to 5.

As illustrated in the formulae (f), (h), (j), and (l), a polymer according to the present embodiment has a benzocyclobutene structure and can be heated to produce a cross-linked compound. The cross-linked compound has a sufficiently low linear expansion coefficient of 60 ppm/° C. or less. Because of its small dimensional change with temperature, the cross-linked compound can be suitably used as a material for optical elements and electric circuit boards.

Furthermore, the cross-linking of a polymer according to the present embodiment does not produce by-products, such as ethylene. Thus, the polymer can be formed into a product without air bubbles. The cross-linking of a polymer according to the present embodiment does not require a cross-linker or a cross-linking aid.

The molecular weight of a polymer according to the present embodiment is, but not limited to, 1000 or more and 1,000,000 or less, preferably 3000 or more and 500,000 or less, more preferably 3000 or more and 7000 or less, in terms of weight-average molecular weight (Mw). The molecular weight is a polystyrene equivalent as measured by gel permeation chromatography (GPC).

In a polymer according to the present embodiment, the moieties having the direct bond (x1), the formulae (x2) to (x5), the formula (x10), the formula (x11), the direct bond (w1), the formulae (w2) to (w5), the formula (w10), the formula (w11), the direct bond (v1), the formulae (v2) to (v5), the formula (v10), the formula (v11), the direct bond (u1) the formulae (u2) to (u5), the formula (u10), and the formula (u11) have no oxygen atom, resulting in low water absorbency. The moieties having the formulae (x6) to (x12), the formulae (w6) to (w12), the formulae (v6) to (v12), and the formulae (u6) to (u12) have a heteroatom, resulting in good adhesion with a substrate made of a metal, such as copper, or glass.

A polymer according to the present embodiment may be a copolymer that has a second constitutional repeating unit other than the constitutional repeating unit described above provided that the advantages of the present invention are secured. Examples of the second constitutional repeating unit are as follows:

[Chem. 42]

(3-1)
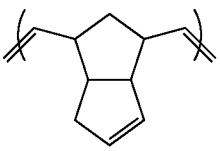

(3-2)

(3-3)
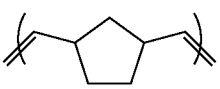

(3-4)

(3-5)
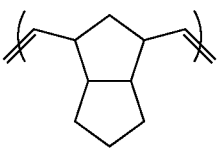

(3-6)
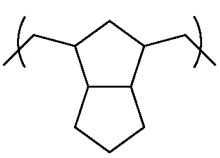

(3-7)
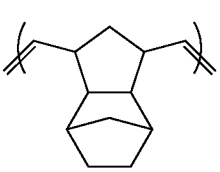

(3-8)
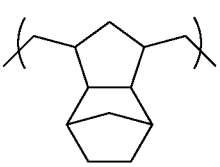

(3-9)
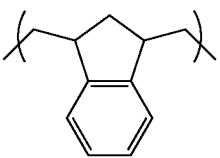

(3-10)
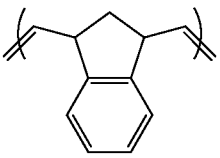

(3-11)
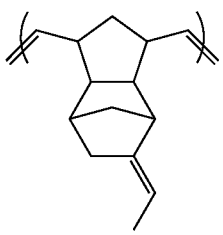

(3-12)
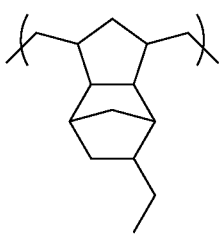

(3-13)
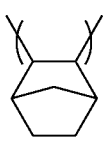

(3-14)
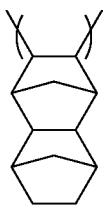

(3-15)
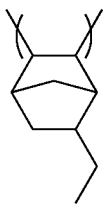

In the case that a polymer according to the present embodiment is a copolymer, the molar ratio of the constitutional repeating unit represented by one of the formulae (e1) to (e3), the formulae (g1) to (g3), the formulae (i1) to (i3), the formulae (k1) to (k3) to the second constitutional repeating unit represented by one of the formulae (3-1) to (3-15) is preferably in the range of 5:95 to 95:5, more preferably 30:70 to 40:60. The optical properties, such as transmittance, refractive index, and Abbe number, can be controlled by the percentage of the second constitutional repeating unit having one of the formulae (3-1) to (3-15) in a polymer according to the present embodiment.

A copolymer according to the present embodiment may be a random copolymer, a block copolymer, or an alternating copolymer.

Examples of a polymer according to the present embodiment are as follows:

[Chem. 43]

(3-17)
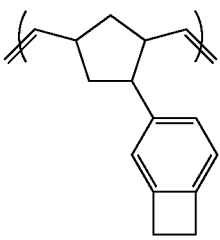

(3-18)
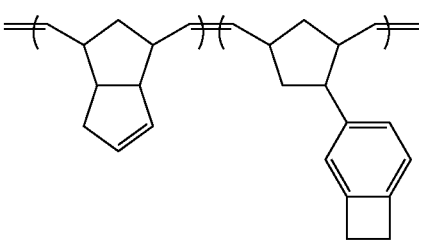

(3-19)
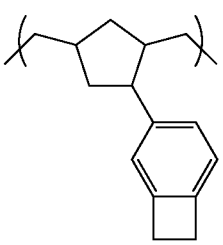

Cross-Linked Compound

A cross-linked compound according to the present embodiment has the following general formula (III).

$$M\text{-}R\text{-}T\text{-}R'\text{-}M' \quad (III)$$

In the formula (III), M and M' are polymers having a constitutional repeating unit represented by one of the formulae (m1) to (m12), each of R and R' is a direct bond (r1) or has one of the formulae (r2) to (r12), and T has the formula (t).

[Chem. 44]

(m1)
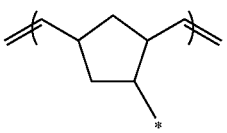

(m2)
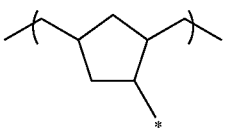

(m3)
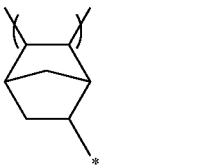

(m4) 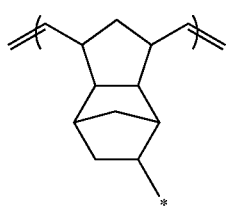
(m5) 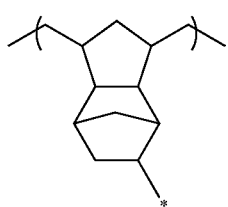
(m6) 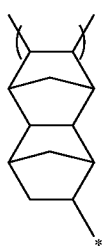
(m7) 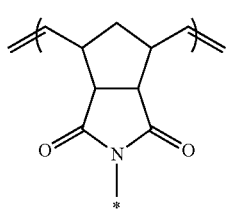
(m8) 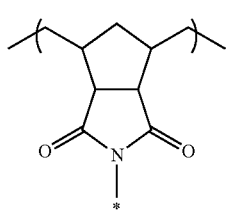
(m9) 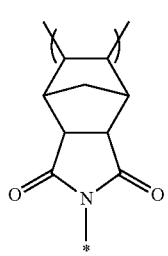
(m10) 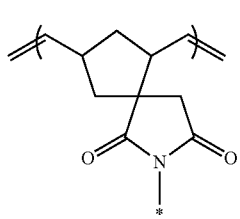
(m11) 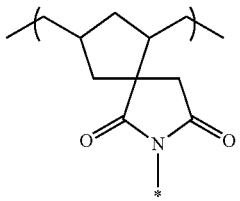
(m12) 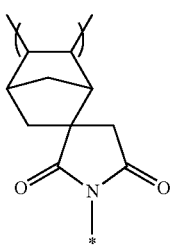
In the formulae (m1) to (m12), * denotes a bonding arm and is bonded to R or R' of the formula (III).
[Chem. 45]
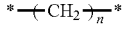 (r2)
 (r3)
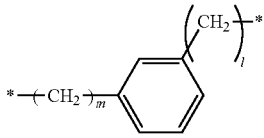 (r4)
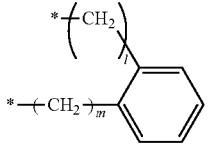 (r5)
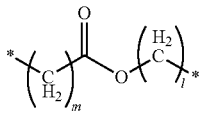 (r6)
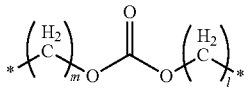 (r7)
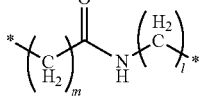 (r8)
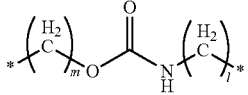 (r9)

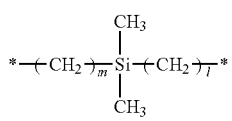
(r10)

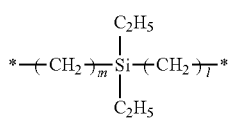
(r11)

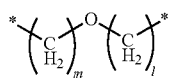
(r12)

In each of the formulae (r2) to (r12), two *'s denote a bonding arm and are bonded to M or M' or T of the formula (III), and n, m, and l independently denote an integer of 0 to 5.

[Chem 46]

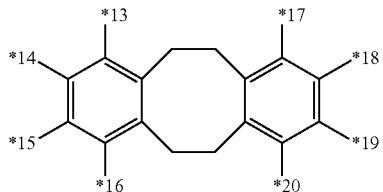
(t)

In the formula (t), *13 to *20 denote a bonding arm, one of *13 to *16 and one of *17 to *20 are bonded to M and M' of the formula (III), and the remainder of *13 to *20 not bonded to M or M' of the formula (III) are bonded to a hydrogen atom.

A cross-linked compound according to the present embodiment has a sufficiently low linear expansion coefficient of 60 ppm/° C. or less. Because of its small dimensional change with temperature, the cross-linked compound can be suitably used as a material for optical elements and electric circuit boards. As described above, a cross-linked compound according to the present embodiment can be produced by heating, and the production of the cross-linked compound requires no cross-linker or cross-linking aid. The production of a cross-linked compound according to the present embodiment does not produce by-products, such as ethylene. Thus, the cross-linked compound provides a product without air bubbles.

In a cross-linked compound according to the present embodiment, the moieties having the direct bond (r1), the formulae (r2) to (r5), the formula (r10), and the formula (r11) have no oxygen atom, resulting in low water absorbency. The moieties having the formulae (r6) to (r12) have a heteroatom, resulting in good adhesion with a substrate made of a metal, such as copper, or glass.

Because of its small dimensional change with temperature, a cross-linked compound according to the present embodiment can be suitably used as a material for optical elements, such as lenses, light guide plates, protective films, deflection films, retardation films, and touch panels, transparent electrode substrates, optical recording substrates, such as CDs, MDs, and DVDs, electric circuit boards, such as TFT substrates, and electronic components, such as color filter substrate sealants, prepregs, resin-coated copper foil, printed wiring boards, insulating sheets, interlayer insulating films, antenna substrates, electromagnetic wave absorbers, and electromagnetic shields.

The cross-linked structure of a cross-linked compound according to the present embodiment can be identified by a known method. More specifically, the cross-linked compound can be subjected to infrared (IR) spectroscopy to observe a peak of a benzocyclobutene skeleton around 1470 $cm^{-1}$, which is reduced by a cross-linking reaction, and a peak around 1500 $cm^{-1}$, which appears due to the cross-linking reaction.

Examples of a cross-linked compound according to the present embodiment are as follows:

[Chem. 47]

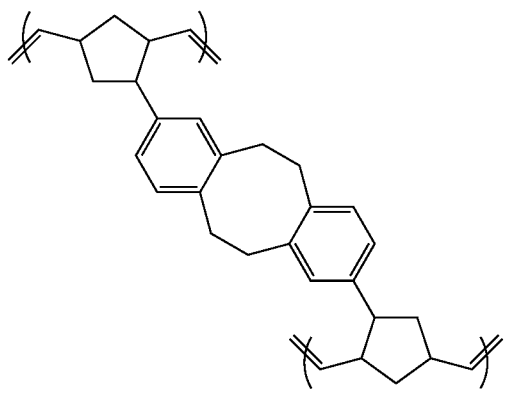
(4-1)

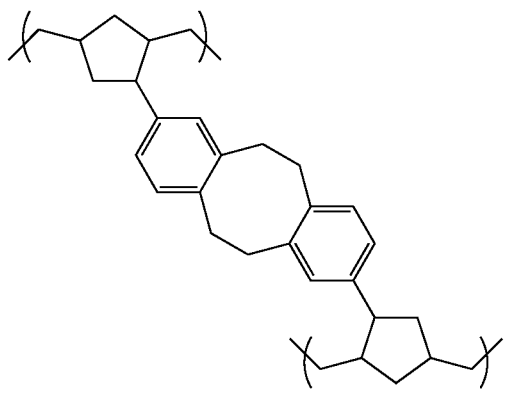
(4-2)

(4-3)
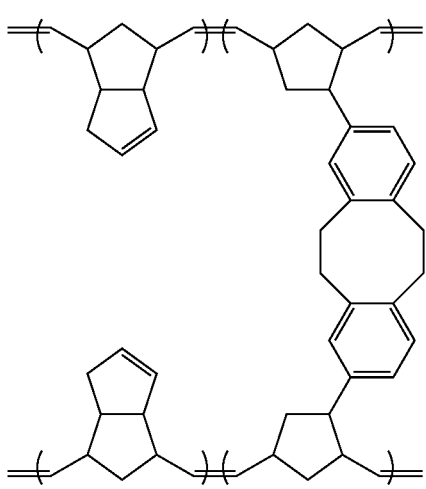
(4-4)
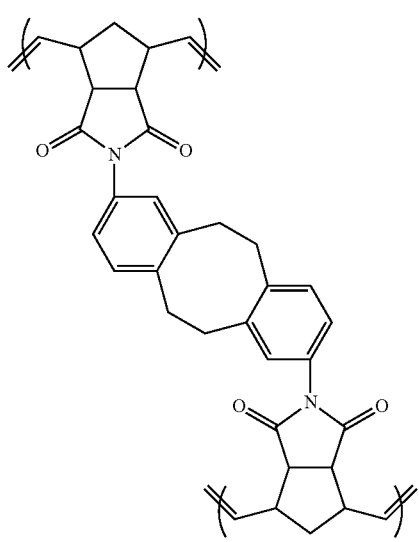
(4-5)
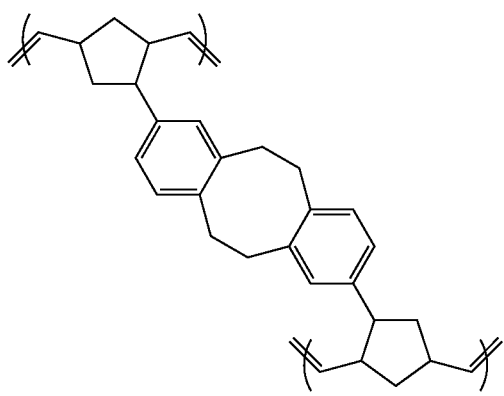
(4-6)
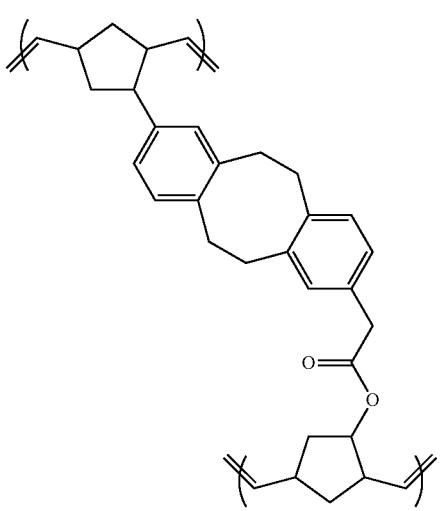
(4-7)
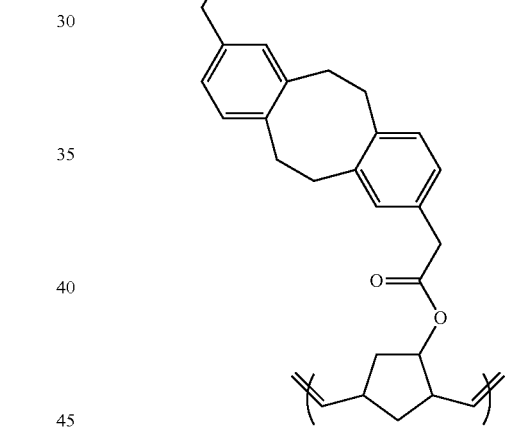
A cross-linked compound according to the present embodiment may be a cross-linked compound between the polymer described above and another polymer having a benzocyclobutene ring. The polymer having a benzocyclobutene ring is not particularly limited and may have the following constitutional repeating unit.
[Chem. 48]
(5-1)
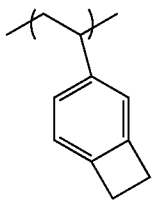

-continued

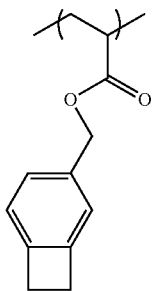
(5-2)

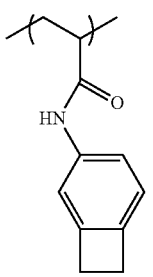
(5-3)

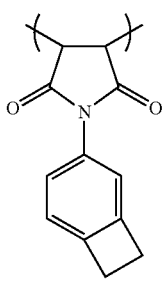
(5-4)

Examples of the cross-linked compound between the polymer described above and another polymer having a benzocyclobutene ring are as follows:

[Chem. 49]

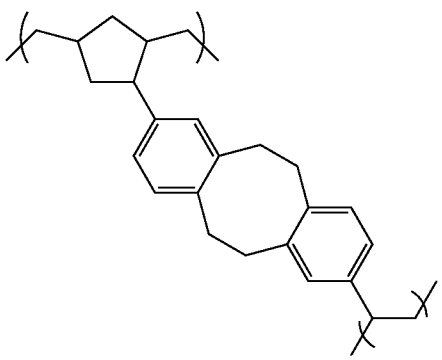
(5-5)

Method for Producing Compounds

A compound according to the present embodiment can be easily synthesized by the following methods.

Compound Having General Formula (I)

A compound having the general formula (I) can be synthesized by a Diels-Alder reaction between cyclopentadiene and a benzocyclobutene having a vinyl group. The reaction can be directed to the formula (b1) or the formula (b2) depending on the amount of cyclopentadiene (FIG. 1).

Compound Having General Formula (II) in which D is (d1)

Figure 2A:
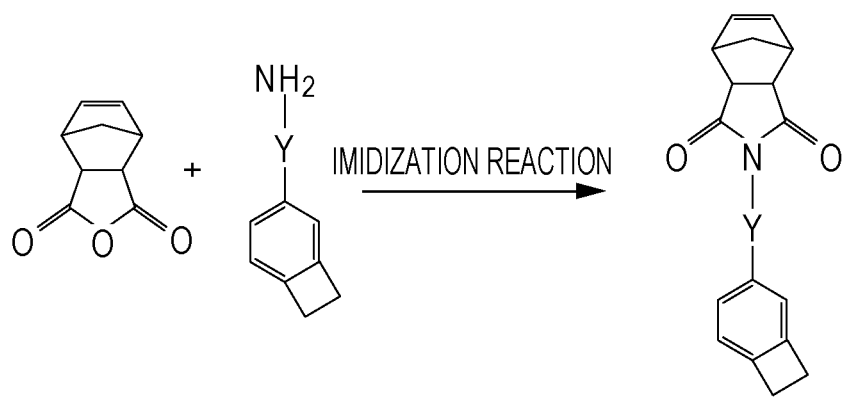
FIGS. 2A and 2B are reaction schemes in a method for producing a compound according to an embodiment of the present invention.
Figure 2B:
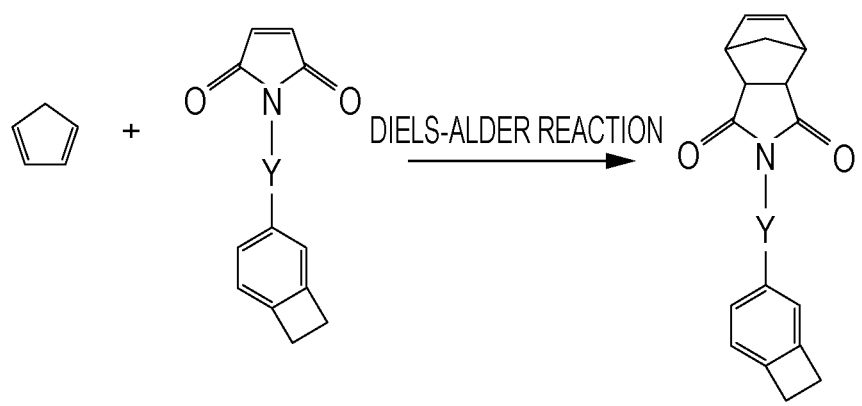

A compound having the general formula (II) in which d is (d1) can be synthesized by an imidization reaction between 5-norbornene-2,3-dicarboxylic anhydride and a benzocyclobutene having an amino group (FIG. 2A) or a Diels-Alder reaction between cyclopentadiene and a benzocyclobutene having a N-substituted maleimide group (FIG. 2B).

Compound Having General Formula (II) in which D is (d2)

Figure 3A:
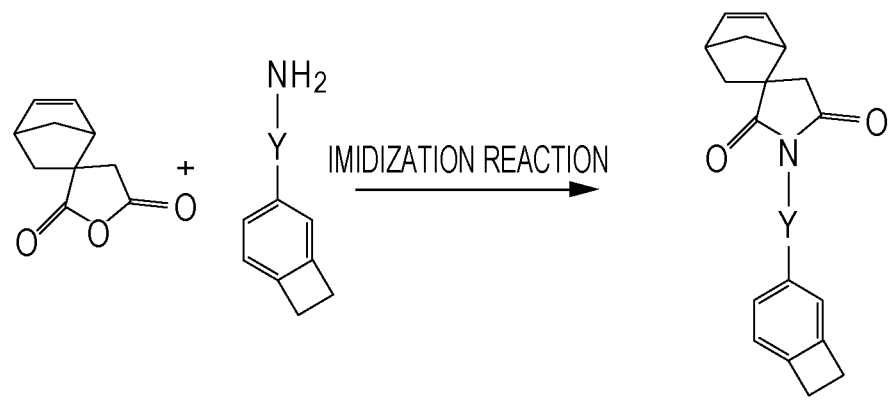
FIGS. 3A and 3B are reaction schemes in a method for producing a compound according to an embodiment of the present invention.
Figure 3B:
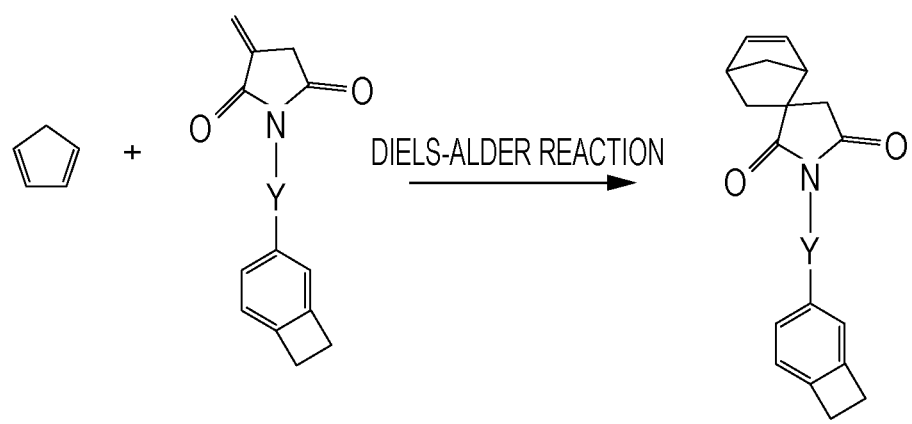

A compound having the general formula (II) in which d is (d2) can be synthesized by an imidization reaction between a cyclopentadiene-itaconic anhydride adduct and a benzocyclobutene having an amino group (FIG. 3A) or a Diels-Alder reaction between cyclopentadiene and a benzocyclobutene having a N-substituted itaconic acid imide group (FIG. 3B).

Method for Producing Polymer

A method for producing a polymer according to the present embodiment involves (i) ring-opening metathesis polymerization, (ii) ring-opening metathesis polymerization and subsequent hydrogenation reaction, or (iii) addition polymerization of the compound described above.

(i) Ring-Opening Metathesis Polymerization

In the ring-opening metathesis polymerization, the compound described above is brought into contact with a ring-opening metathesis polymerization catalyst.

The ring-opening metathesis polymerization catalyst may be any catalyst that can promote the ring-opening metathesis polymerization of the compound.

Examples of the ring-opening metathesis polymerization catalyst include (a) group 4-8 transition metal carbene complex catalysts and (b) combinations of a transition metal compound and an alkylating agent or Lewis acid functioning as a promoter.

Specific examples of the catalyst (a) include tungsten alkylidene complexes, such as W(N-2,6-i-Pr$_2$C$_6$H$_3$)(CH-t-Bu)(O-t-Bu)$_2$, W(N-2,6-i-Pr$_2$C$_6$H$_3$)(CH-t-Bu)(OCMe$_2$CF$_3$)$_2$, W(N-2,6-i-Pr$_2$C$_6$H$_3$)(CH-t-Bu)(OCMe(CF$_3$)$_2$)$_2$, W(N-2,6-i-Pr$_2$C$_6$H$_3$)(CHCMe$_2$Ph)(O-t-Bu)$_2$, W(N-2,6-i-Pr$_2$C$_6$H$_3$)(CHCMe$_2$Ph)(OCMe$_2$CF$_3$)$_2$, and W(N-2,6-i-Pr$_2$C$_6$H$_3$)(CHCMe$_2$Ph)) OCMe (CF$_3$)$_2$)$_2$, molybdenum alkylidene complexes, such as Mo(N-2,6-i-Pr$_2$C$_6$H$_3$)(CH-t-Bu)(O-t-Bu)$_2$, Mo(N-2,6-i-Pr$_2$C$_6$H$_3$)(CH-t-Bu)(OCMe$_2$CF$_3$)$_2$, Mo(N-2,6-i-Pr$_2$C$_6$H$_3$)(CH-t-Bu)(OCMe (CF$_3$)$_2$)$_2$, Mo(N-2,6-i-Pr$_2$C$_6$H$_3$)(CHCMe$_2$Ph)(o-t-Bu)$_2$, MO (N-2,6-i-Pr$_2$C$_6$H$_3$)(CHCMe$_2$Ph)(OCMe$_2$CF$_3$)$_2$, Mo(N-2,6-i-Pr$_2$C$_6$H$_3$)(CHCMe$_2$Ph)) OCMe (CF$_3$)$_2$)$_2$, Mo(N-2,6-i-Pr$_2$C$_6$H$_3$)(BIPHEN), and Mo(N-2,6-i-Pr$_2$C$_6$H$_3$)(BINO)(THF), and ruthenium carbene complexes, such as bis(tricyclohexylphosphine)benzylidene ruthenium dichloride, bis(triphenylphosphine)-3,3-diphenylpropenylidene ruthenium dichloride, bis(1,3-diisopropylimidazolidine-2-ylidene)benzylidene ruthenium dichloride, bis(1,3-dicyclohexylimidazolidine-2-ylidene)benzylidene ruthenium dichloride, bis(1,3-diisopropyl-4-imidazoline-2-ylidene)benzylidene ruthenium dichloride, bis(1,3-dicyclohexyl-4-imidazoline-2-ylidene)benzylidene ruthenium dichloride, (1,3-dicyclohexylimidazolidine-2-ylidene)(tricyclohexylphosphine)benzylidene ruthenium dichloride, (1,3-dicyclohexyl-4-imidazoline-2-ylidene)(tricyclohexylphosphine) benzylidene ruthenium dichloride, (1,3-dimesitylimidazolidine-2-ylidene)(tricyclohexylphosphine) benzylidene ruthenium dichloride, (1,3-dimesityl-4-imidazoline-2-ylidene)(tricyclohexylphosphine) benzylidene ruthenium dichloride, and [1,3-di(1'-phenylethyl)-4-imidazoline-2-ylidene](tricyclohexylphosphine)benzylidene ruthenium dichloride, wherein Me denotes a methyl group, i-Pr denotes an isopropyl group, t-Bu denotes a tert-butyl group, Ph denotes a phenyl group, BIPHEN denotes 3,3'-Di-tert-butyl-5,5',6,6'-tetramethyl-1,1'-biphenyl-2,2'-diol, BINO denotes 1,1'-binaphthalene-2,2'-dioxy, and THF denotes tetrahydrofuran.

Specific examples of the transition metal compound in (b) include $MoCl_4$, $MoBr_2$, $MoBr_3$, $MoBr_4$, $WCl_2$, $WBr_2$, $WCl_4$, $WBr_4$, $WCl_5$, and $WBr_5$.

Examples of the alkylating agent functioning as a promoter in (b) include methyl lithium, ethyl lithium, n-butyl lithium, methyl magnesium chloride, and methyl magnesium bromide. Examples of the Lewis acid functioning as a promoter in (b) include trimethyl aluminum, triethyl aluminum, triisopropyl aluminum, tetramethyl tin, tetraethyl tin, and tetrabutyl tin.

Group 4-8 transition metal carbene complex catalysts, in particular, ruthenium carbene complex catalysts have high catalytic activity.

The molar ratio of the ring-opening metathesis polymerization catalyst to the compound is generally in the range of 1:100 to 1:1,000,000, preferably 1:1000 to 1:500,000. An excessively large amount of polymerization catalyst is difficult to remove. An excessively small amount of polymerization catalyst results in insufficient polymerization activity.

The polymerization temperature is generally, but not limited to, −30° C. or more and 200° C. or less, preferably 0° C. or more and 180° C. or less.

The polymerization time is generally, but not limited to, 1 minute or more and 50 hours or less.

Although the ring-opening metathesis polymerization reaction may be performed in the absence of solvent, it may be performed in the presence of an organic solvent so as to reduce an increase in viscosity during the polymerization reaction.

Specific examples of the organic solvent include aliphatic hydrocarbon solvents, such as pentane, hexane, and heptane, alicyclic hydrocarbon solvents, such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, hexahydroindene, and cyclooctane, aromatic hydrocarbon solvents, such as benzene, toluene, and xylene, nitrogen-containing hydrocarbon solvents, such as nitromethane, nitrobenzene, and acetonitrile, and ether solvents, such as diethyl ether and tetrahydrofuran.

For polymerization in the organic solvent, the concentration of the cyclic olefin monomer is preferably 1% by mass or more and 60% by mass or less, more preferably 5% by mass or more and 40% by mass or less, of the organic solvent. When the concentration of the cyclic olefin monomer is less than 1% by mass, this results in low productivity. When the concentration of the cyclic olefin monomer is more than 60% by mass, this results in an increased viscosity of the solution after polymerization, resulting in poor handleability.

A molecular weight modifier may be used to control the molecular weight of the polymer. Specific examples of the molecular weight modifier include α-olefins, such as 1-butene, 1-pentene, 1-hexene, and 1-octene; styrenes, such as styrene and vinyltoluene; ethers, such as ethyl vinyl ether, i-butyl vinyl ether, and allyl glycidyl ether; halogen-containing vinyl compounds, such as allyl chloride; oxygen-containing vinyl compounds, such as allyl acetate, allyl alcohol, and glycidyl methacrylate; and nitrogen-containing vinyl compounds, such as acrylamide.

The amount of molecular weight modifier may be 0% by mole or more and 100% by mole or less of the compound.

(ii) Ring-Opening Metathesis Polymerization and Subsequent Hydrogenation Reaction The ring-opening metathesis polymerization is described above. After the ring-opening metathesis polymerization of the compound, a hydrogenation reaction is performed in the presence of a hydrogenation catalyst and hydrogen to hydrogenate a carbon-carbon double bond of the resulting polymer. A product of the hydrogenation reaction is referred to as a hydrogenated product.

The hydrogenation catalyst may be any catalyst generally used in hydrogenation reactions of olefins and aromatic compounds. Specific examples of the hydrogenation catalyst include (a) supported metal catalysts, for example, a transition metal, such as palladium, platinum, nickel, rhodium, or ruthenium, supported on a carrier, such as carbon, alumina, silica, or diatomaceous earth, (b) homogeneous catalysts composed of an organic transition metal compound containing titanium, cobalt, or nickel and an organic metal compound containing lithium, magnesium, aluminum, or tin, and (c) homogeneous catalysts composed of a metal complex catalyst containing rhodium or ruthenium.

Specific examples of the hydrogenation catalyst (a) include nickel/silica, nickel/diatomaceous earth, nickel/alumina, palladium/carbon, palladium/silica, palladium/diatomaceous earth, palladium/alumina, platinum/silica, platinum/alumina, rhodium/silica, rhodium/alumina, ruthenium/silica, and ruthenium/alumina.

Specific examples of the hydrogenation catalyst (b) include cobalt acetate/triethyl aluminum, nickel acetylacetonate/triisobutyl aluminum, titanocene dichloride/n-butyl lithium, zirconocene dichloride/sec-butyl lithium, and tetrabutoxy titanate/dimethyl magnesium.

Specific examples of the hydrogenation catalyst (c) include dihydridotetra(triphenylphosphine)ruthenium, dihydrido(acetonitrile)tris(triphenylphosphine)ruthenium, and dihydrido(tetrahydrofuran)tris(triphenylphosphine)ruthenium.

The conditions suitable for the hydrogenation reaction depend on the type of hydrogenation catalyst. The hydrogenation temperature is generally −20° C. or more and 250° C. or less, preferably 0° C. or more and 220° C. or less, more preferably 20° C. or more and 200° C. or less. The hydrogen pressure is generally 0.01 MPa or more and 10 MPa or less, preferably 0.05 MPa or more and 7 MPa or less, more preferably 0.1 MPa or more and 5 MPa or less. An excessively low hydrogenation temperature results in a low reaction rate, and an excessively high hydrogenation temperature induces a side reaction. An excessively low hydrogen pressure results in a low hydrogenation rate, and an excessively high hydrogen pressure requires a high-pressure reaction apparatus.

The hydrogenation reaction time is generally, but not limited to, in the range of 1 minute to 50 hours.

The hydrogenation reaction is generally performed in an inert organic solvent. The type of organic solvent depends on the solubility of a hydrogenated product. Examples of the solvent include aromatic hydrocarbons, such as benzene and toluene; aliphatic hydrocarbons, such as n-pentane and n-hexane; alicyclic hydrocarbons, such as cyclohexane and decalin; and ethers, such as tetrahydrofuran and ethylene glycol dimethyl ether. Examples of a solvent having excellent solubility for a hydrogenated product of cyclic olefin ring-opening polymerization used in the present invention include hydrocarbon solvents and ethers, typically alicyclic hydrocarbon solvents.

The organic solvent may generally be the same as the polymerization reaction solvent. Thus, a hydrogenation catalyst may be directly added to the polymerization reaction solution.

The hydrogenation catalyst may be removed by the following methods.

In the case of a homogeneous catalyst, an oxidizing agent or a basic compound and a poor solvent for the reaction solution, such as water or methanol, are added to the reaction solution after polymerization to convert the homogeneous catalyst into a metal oxide or a metal salt, the metal oxide or the metal salt is extracted into the poor solvent, and the homogeneous catalyst is removed by filtration or centrifugation. Alternatively, the homogeneous catalyst is removed by adsorption on an adsorbent or extraction into an aqueous solution of an acid, such as hydrochloric acid.

In the case of a supported hydrogenation catalyst, it can be easily removed by centrifugation or filtration.

(iii) Addition Polymerization

In the addition polymerization, the compound described above is brought into contact with an addition polymerization catalyst.

The addition polymerization catalyst may be any catalyst that can promote the addition polymerization of the compound.

Examples of the addition polymerization catalyst include (a) group 4-6 transition metal catalysts and (b) group 8-10 transition metal catalysts.

Specific examples of the addition polymerization catalyst (a) include Ziegler-Natta catalysts containing $TiCl_3$ or $TiCl_4$; metallocene catalysts containing an organometallic complex, such as $(C_5H_5)_2TiCl_2$, $(C_5H_5)_2ZrCl_2$, or $(C_5H_5)_2Zr(CH_3)_2$; and half-metallocene catalysts containing an organic metal, such as $(C_5H_4Si(CH_3)_3)Sc(Si(CH_3)_3)_2$.

Specific examples of the addition polymerization catalyst (b) include cobalt compounds, such as cobalt (II) acetate, cobalt (II) acetylacetonate, cobalt (II) tetrafluoroborate, cobalt chloride, and cobalt (II) benzoate; nickel compounds, such as nickel acetate, nickel acetylacetonate, nickel carbonate, nickel chloride, nickel ethylhexanoate, nickelocene, $NiCl_2[P(C_6H_5)_3]_2$, bisallyl nickel, and nickel oxide; and palladium compounds, such as palladium chloride, palladium bromide, palladium oxide, $PdCl_2[P(C_6H_5)_3]_2$, $PdCl_2(C_6H_5CN)_2$, $PdCl_2(CH_3CN)_2$, $[Pd(CH_3CN)_4][BF_4]_2$, $[Pd(C_2H_5CN)_4][BF_4]_2$, palladium acetylacetonate, and palladium acetate.

These catalysts may be used in combination with a promoter. Examples of the promoter include aluminoxanes, such as methylaluminoxane and polyisobutylaluminoxane; boron compounds, such as $B(C_6F_5)_3$, $BF_3 \cdot (C_2H_5)_2O$, $[C_6H_5NH(CH_3)_2]^+[B(C_6F_5)_4]^-$, $[(C_6H_5)_3C]^+[B(C_6F_5)_4]^-$, $Li^+[B(C_6F_5)_4]^-$, and $Na^+[B(3,5-(CF_3)_2C_6H_3)]_4^-$; phosphine compounds, such as tricyclopentylphosphine, dicyclopentyl(isopropyl)phosphine, dicyclopentylphenylphosphine, dicyclopentylcyclooctylphosphine, tricyclohexylphosphine, dicyclohexyl(isopropyl)phosphine, tri(tert-butyl)phosphine, dicyclohexyl(tert-butyl)phosphine, dicyclohexylphenylphosphine, dicyclohexyl(2-ethylhexyl)phosphine, and dicyclohexyl(o-tolyl)phosphine. These promoters may be used alone or in combination.

The molar ratio of the addition polymerization catalyst to the compound described above is generally in the range of 1:100 to 1:1,000,000, preferably 1:1000 to 1:500,000. An excessively large amount of addition polymerization catalyst is difficult to remove. An excessively small amount of addition polymerization catalyst results in insufficient polymerization activity.

The polymerization temperature is generally, but not limited to, −30° C. or more and 200° C. or less, preferably 0° C. or more and 180° C. or less. The polymerization time is generally, but not limited to, 1 minute or more and 50 hours or less.

Although the addition polymerization reaction may be performed in the absence of solvent, it may be performed in the presence of an organic solvent so as to reduce an increase in viscosity during the polymerization reaction.

Specific examples of the organic solvent include aliphatic hydrocarbon solvents, such as pentane, hexane, and heptane, alicyclic hydrocarbon solvents, such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, hexahydroindene, and cyclooctane, aromatic hydrocarbon solvents, such as benzene, toluene, and xylene, nitrogen-containing hydrocarbon solvents, such as nitromethane, nitrobenzene, and acetonitrile, and ether solvents, such as diethyl ether and tetrahydrofuran.

For polymerization in the organic solvent, the concentration of the compound described above is preferably 1% by mass or more and 60% by mass or less, more preferably 5% by mass or more and 40% by mass or less, of the organic solvent. When the concentration of the compound is less than 1% by mass, this results in low productivity. When the concentration of the compound is more than 60% by mass, this results in an increased viscosity of the solution after polymerization, resulting in poor handleability.

A molecular weight modifier may be used to control the molecular weight of the polymer. Examples of the molecular weight modifier include α-olefins, such as ethylene, propene, 1-butene, 1-pentene, 1-hexene, 1-octene, 1-nonene, and 1-decene; compounds having a cyclopentene ring, such as cyclopentene, 3-methylcyclopentene, 3-ethylcyclopentene, 3-isopropylcyclopentene, 3-n-propylcyclopentene, 4-methylcyclopentene, 4-ethylcyclopentene, 4-isopropylcyclopentene, and 4-phenylcyclopentene; and compounds having a cycloalkane diene ring, such as cycloocta-1,5-diene, 3-methylcycloocta-1,5-diene, 3-ethylcycloocta-1,5-diene, cycloocta-1,4-diene, and cyclohexa-1,4-diene.

The amount of molecular weight modifier may be 0% by mole or more and 100% by mole or less of the compound.

Method for Producing Cross-Linked Compound

A method for producing a cross-linked compound according to the present embodiment involves heat treatment and/or microwave irradiation treatment of the polymer described above.

The heating temperature of the heat treatment may be any temperature at which the benzocyclobutene ring of the polymer opens and is preferably 180° C. or more and 400° C. or less, more preferably 200° C. or more and 300° C. or less. A cross-linking temperature of 180° C. or more results in sufficient cross-linking and a sufficiently low linear expansion coefficient. A cross-linking temperature of 400° C. or less can reduce the thermal decomposition of the polymer and the cross-linked compound.

The frequency of a microwave in the microwave irradiation treatment may be any frequency at which the benzocyclobutene ring of the polymer opens, for example, 2.45 or 5.8 GHz. More specifically, the frequency of the microwave may be 2,450±50 MHz in the 2.45 GHz band or 5,800±75 MHz in the 5.8 GHz band, both of which are the industrial, scientific, and medical (ISM) bands. The microwave irradiation may be performed more than once under different conditions. The microwave irradiation temperature is preferably, but not limited to, 50° C. or more and 400° C. or less, more preferably 80° C. or more and 300° C. or less, particularly preferably 100° C. or more and 200° C. or less.

The heat treatment and the microwave irradiation treatment may be performed simultaneously or sequentially (in any order).

The time of the heat treatment and the microwave irradiation treatment is not particularly limited provided that the polymer can be cross-linked, for example, 1 minute or more and 10 hours or less. A cross-linking time of less than 1 minute may result in insufficient cross-linking, thus reducing the advantages of the present invention. A cross-linking time of more than 10 hours may result in low productivity or, in the heat treatment, the degradation of the cross-linked compound.

In order to prevent the oxidative degradation of the cross-linked compound, the heat treatment and/or the microwave irradiation treatment may be performed in an inert atmosphere, such as an argon, helium, or nitrogen atmosphere.

Second Embodiment

Optical Element

Figure 4A:
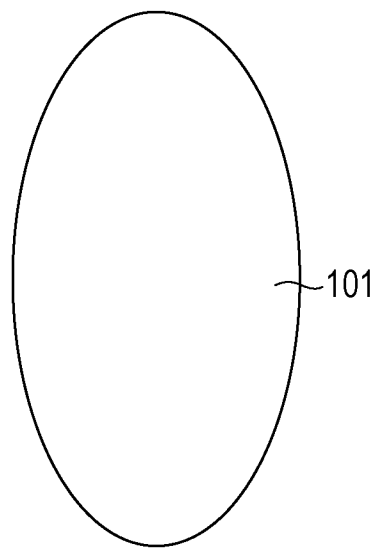
FIGS. 4A and 4B are schematic views of an optical element according to an embodiment of the present invention.
Figure 4B:
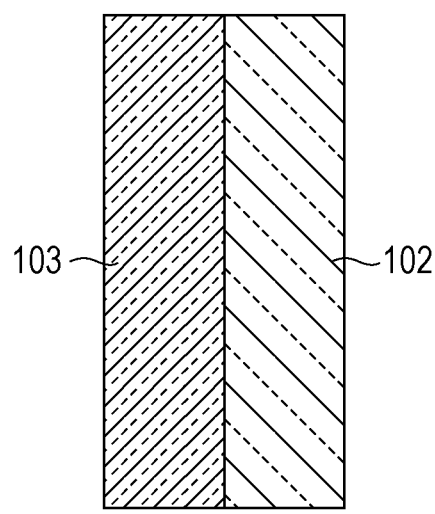

In a second embodiment, an optical element is described with reference to FIGS. 4A and 4B. FIG. 4A illustrates an optical element, such as a convex lens, that includes an organic transparent member 101 containing the cross-linked compound described above. FIG. 4B illustrates an optical element that includes an organic transparent member 102 on a substrate 103. The organic transparent member 102 contains the cross-linked compound, and the substrate 103 contains an inorganic material, such as glass. An optical element according to the present embodiment contains a cross-linked compound having a low linear expansion coefficient of 60 ppm/° C. or less and exhibits a small dimensional change with temperature. An optical element according to the present embodiment has a cyclic olefin polymer structure that includes a constitutional repeating unit represented by one of the formulae (m1) to (m12) and therefore has high visible light transmittance and low water absorbency.

The organic transparent members 101 and 102 may contain an antioxidant and/or a light stabilizer depending on the type of cross-linked compound.

The antioxidant may be any antioxidant that can prevent the oxidative degradation of the cross-linked compound, for example, a phenol antioxidant, such as an alkyl-substituted phenol antioxidant, a phosphite antioxidant, or a sulfur antioxidant. The antioxidant can prevent coloring or strength reduction resulting from oxidative degradation during a forming process without causing deterioration in transparency and heat resistance.

The light stabilizer may be any light stabilizer that can prevent photodegradation of the cross-linked compound, for example, a benzophenone light stabilizer, a benzotriazole light stabilizer, or a hindered amine light stabilizer. A hindered amine light stabilizer provides excellent transparency and anti-coloring.

Examples of an optical element according to the present embodiment include optical lenses and optical prisms, such as image pickup lenses for cameras, lenses for microscopes, endoscopes, and telescopes, and transmission lenses, including spectacle lenses; pickup lenses for optical disks, such as CDs, CD-ROMs, write-once read-many (WORM) optical disks, magneto-optical (MO) disks, MiniDisc (MD, Trade name), and digital versatile disks (DVD); and lenses for scanning optical systems, such as lenses for laser scanning systems, including fθ lenses and sensor lenses for laser beam printers, and prismatic lenses for camera finders. Other examples of an optical element according to the present embodiment include light guide plates for liquid crystal displays; optical films, such as polarizing films, retardation films, and light diffusion films; light diffusion plates; optical cards; and liquid crystal display element substrates.

An optical element according to the present embodiment may be one of the lenses described above. The lens may have an anti-reflection film on its surface and an intermediate layer between the anti-reflection film and the optical element. The anti-reflection film is not particularly limited and may have a refractive index close to the refractive index of the lens. The intermediate layer is not particularly limited and may have a refractive index between the refractive index of the lens and the refractive index of the anti-reflection film. In order to reduce internal reflection in the lens, a film that is opaque in an operating wavelength region may be formed on a portion that blocks light, typically the lens edge.

The organic transparent members 101 and 102 may contain a generally available resin. Examples of the generally available resin include commercially available resins, such as polyethylenes, polyisoprenes, polystyrenes, polyacrylates, polycarbonates, polyesters, polyethers, polyamides, and cycloolefin polymers.

The organic transparent members 101 and 102 may contain a filler so as to improve the mechanical characteristics, electrical characteristics, and optical properties of the cross-linked compound. The filler may be an inorganic substance or an organic substance.

The inorganic substance may be a silicon oxide, a metal oxide, a carbon compound, a metal multiple oxide, a metal sulfide, a metal compound semiconductor, or a metal. Examples of the metal oxide include aluminum oxide, titanium oxide, niobium oxide, tantalum oxide, zirconium oxide, zinc oxide, magnesium oxide, tellurium oxide, yttrium oxide, indium oxide, tin oxide, and indium tin oxide. Examples of the carbon compound include diamond, carbon nanotube, graphite, and fullerene. Examples of the metal multiple oxide include lithium niobate, potassium niobate, and lithium tantalate. Examples of the metal compound semiconductor include metal sulfides, such as zinc sulfide and cadmium sulfide, zinc selenide, cadmium selenide, zinc telluride, and cadmium telluride. Examples of the metal include gold. The inorganic substance may be a core-shell inorganic substance in which an inorganic substance is coated with another inorganic component. The inorganic substance may be of any shape, such as spherical, elliptical, flat, or rod-shaped.

In the case that an optical element according to the present embodiment needs to be transparent, the inorganic substance preferably has an average primary particle size of 30 nm or less, more preferably 10 nm or less, so as to prevent light scattering. The term "average primary particle size", as used herein, refers to a particle size measured with a transmission electron microscope (TEM).

Examples of the organic substance include wood flour, starch, organic pigments, polystyrene, nylon, polyolefins, such as polyethylene and polypropylene, vinyl chloride, elastomers, and waste plastics.

Examples of the filler include the inorganic and organic substances described above and short and long fibers, such as chopped strands and milled fibers. Examples of the fibers include inorganic fibers, such as glass fibers, carbon fibers, and metal fibers; and organic fibers, such as aramid fibers, nylon fibers, jute fibers, kenaf fibers, bamboo fibers, polyethylene fibers, drawn polyethylene fibers, polypropylene fibers, and drawn polypropylene fibers.

The filler may be a flame retardant. Examples of the flame retardant include flame retardants containing an inorganic substance, such as a metal hydroxide, and flame retardants containing an organic substance, such as a phosphorus-containing compound, a halogen-containing compound, or a nitrogen-containing compound. Flame retardants containing a metal hydroxide have a reduced load on the environment. Examples of the flame retardants containing a metal hydroxide include aluminum hydroxide, magnesium hydroxide, basic magnesium oxide, and dawsonite.

A cross-linked compound according to the present embodiment may contain common additive agents, such as an antioxidant, a neutralizing agent, a lubricant, an antistatic agent, a whitening agent, a heat stabilizer, a light stabilizer, a plasticizer, a colorant, an impact modifier, an extender, a mold-release agent, a foaming agent, and/or a processing aid. Specific examples of such additive agents may be found in R. Gachter and H. Muller, Plastics Additives Handbook, 4th edition, 1993.

Any additive agent may be used provided that it does not inhibit a cross-linking reaction in a cross-linking process described below. These additive agents may be used alone or in combination.

Method for Manufacturing Optical Element

A method for manufacturing an optical element using the cross-linked compound described above will be described below. An optical element may be manufactured by (a) preparing a cross-linked compound and shaping the cross-linked compound or by (b) the bulk polymerization and cross-linking of the compound in a lens-shaped mold.

In the method (a), the shaping is not particularly limited and may be performed by any method suitable for the shaping of the optical element. Examples of such a shaping method include injection molding, transfer molding, blow molding, rotational molding, vacuum forming, extrusion molding, calendering, solution casting, heat press forming, inflation, and solvent casting.

The optical element may take the shape of a sphere, rod, plate, cylinder, pipe, tube, fiber, film, or sheet.

A method for manufacturing an optical lens as an example of the optical element will be described below.

An optical lens is manufactured by a process of forming the cross-linked compound into a desired lens shape and a process of cross-linking the formed product.

The process of forming a desired lens shape is not particularly limited. Melt formed products have low birefringence, high mechanical strength, and high dimensional accuracy. Examples of melt forming include commercially available press forming, commercially available extrusion molding, and commercially available injection molding. Injection molding has excellent formability and high productivity. The molding conditions depend on the intended use or the forming method. The temperature of a polymer in injection molding may be any temperature at which the polymer is not cross-linked, for example, 100° C. or more and 300° C. or less. The molding may be performed in an inert gas or under vacuum. In the temperature range described above, the polymer has moderate flowability during the molding, and the formed product does not have sink marks or strain, has a reduced number of silver streaks caused by the thermal decomposition of the polymer, and is resistant to yellowing. In an inert gas or under vacuum, the degradation or yellowing of the formed product can be significantly reduced.

In the process of cross-linking the formed product, the polymer is injected into a lens-shaped forming die and is preferably heated to a temperature of 180° C. or more and 400° C. or less, more preferably 200° C. or more and 300° C. or less, to open the benzocyclobutene ring of the polymer. The cross-linking time of the formed product is not particularly limited and may be 1 minute or more and 10 hours or less. A cross-linking time of less than 1 minute may result in insufficient cross-linking, thus reducing the advantages of the present invention. A cross-linking time of more than 10 hours may result in low productivity or the degradation of the cross-linked compound. In the cross-linking process, the forming die may be pressed. The pressure is generally 0.1 MPa or more and 50 MPa or less, preferably 3 MPa or more and 20 MPa or less. The cross-linking process may be performed in an inert gas or under vacuum. An excessively low cross-linking temperature results in insufficient cross-linking and a slightly high linear expansion coefficient. An excessively high cross-linking temperature results in the degradation of the polymer and the cross-linked compound. In an inert gas or under vacuum, the degradation or yellowing of the cross-linked compound can be significantly reduced.

In the bulk polymerization and cross-linking of the compound by the method (b), a lens-shaped forming die is charged with the compound and a polymerization catalyst, and optionally a polymerization modifier, a chain transfer agent, an antioxidant, and a filler, and is heated to a predetermined temperature.

The polymerization modifier can control polymerization activity and improve the degree of polymerization. Specific examples of the polymerization modifier include trialkoxy aluminum, triphenoxy aluminum, dialkoxyalkyl aluminum, alkoxydialkyl aluminum, trialkyl aluminum, dialkoxy aluminum chloride, alkoxyalkyl aluminum chloride, dialkyl aluminum chloride, trialkoxy scandium, tetraalkoxy titanium, tetraalkoxy tin, and tetraalkoxy zirconium. These polymerization modifiers may be used alone or in combination.

The predetermined temperature may be any polymerization or cross-linking temperature of the compound and may be 20° C. or more and 200° C. or less for polymerization and 200° C. or more and 300° C. or less for cross-linking. The forming die may be pressed. The pressure is generally 0.5 MPa or more and 50 MPa or less, preferably 3 MPa or more and 20 MPa or less. The polymerization and cross-linking process may be performed in an inert gas or under vacuum. The polymerization time may be 1 minute or more and 50 hours or less. A polymerization time of less than 1 minute may result in a low conversion, thus reducing the advantages of the present invention. A polymerization time of more than 50 hours may result in low productivity. The cross-linking time of the polymer is not particularly limited and may be 1 minute or more and 10 hours or less. A cross-linking time of less than 1 minute may result in insufficient cross-linking, thus reducing the advantages of the present invention. A cross-linking time of more than 10 hours may result in low productivity or the degradation of the cross-linked compound.

EXAMPLES

Although the present invention will be further described in the following examples, the present invention is not limited to these examples. In the examples and comparative examples, the identification of a compound, the molar ratio of constitutional repeating units of a polymer, the hydrogenation percentage, the number-average molecular weight (Mn) and the weight-average molecular weight (Mw), the glass transition temperature, the linear expansion coefficient, and the identification of a cross-linked structure were performed or measured by the following methods.

(1) Identification of Compound, Molar Ratio of Constitutional Repeating Units of Copolymer, and Hydrogenation Percentage 15 mg of a sample was dissolved in 1.1 g of CDCl₃ and was subjected to ¹H NMR measurement with a nuclear magnetic resonance spectrometer JNM-ECA-400 (manufactured by JEOL Ltd.).

(2) Number-Average Molecular Weight (Mn) and Weight-Average Molecular Weight (Mw)

The number-average molecular weight (Mn) and the weight-average molecular weight (Mw) were measured at 40° C. with a gel permeation chromatography (GPC) apparatus (manufactured by Waters Corp.) using two Shodex LF-804 columns (manufactured by Showa Denko K.K.) in series and a developing solvent THF and with a refractive index (RI) detector. The number-average molecular weight (Mn) and the weight-average molecular weight (Mw) were based on polystyrene standards.

(3) Glass Transition Temperature (Tg)

The glass transition temperature (Tg) was measured with a differential scanning calorimeter (DSC7020 manufactured by SII NanoTechnology Inc.) in accordance with JIS K 7121 at a temperature initially of from −30° C. to 170° C. and then from −30° C. to 300° C. at a heating rate of 10° C./min.

(4) Linear Expansion Coefficient

In accordance with a testing method for linear thermal expansion coefficient of plastics by thermomechanical analysis (JIS K 7197), a hardened product was cut into a strip of test specimen having a length of 1 cm, the test specimen was placed in a thermomechanical analysis apparatus (Thermo Plus EVO TMA8310 manufactured by Rigaku Corp.) and was subjected to two cycles of heating and cooling between −40° C. and 150° C. at a heating rate of 5° C./min in a nitrogen stream (100 mL/min), and the mean linear expansion coefficient at a temperature in the range of 0° C. to 40° C. was measured during heating in the second cycle.

(5) Identification of Cross-Linked Structure

The cross-linked structure of a cross-linked compound was identified with a Fourier transform infrared spectrometer (Spectrum One manufactured by PerkinElmer, Inc.) by an ATR (attenuated total reflection) method by determining a decrease in the absorbance of a peak around 1470 cm⁻¹ and an increase in the absorbance of a peak around 1500 cm⁻¹ by the cross-linking reaction.

Example 1

Synthesis of 5-(4-benzocyclobutenyl)-2-norbornene (Formula (2))

A 100-ml autoclave with an agitator was charge with 10 g (77 mmol) of 4-vinylbenzocyclobutene, 4.6 g (35 mmol) of dicyclopentadiene, and 438 mg (2.6 mmol) of 4-tert-butylcatechol and was then tightly closed. The reactants were allowed to react at 170° C. for two hours while stirring at 300 rpm. The product was then cooled and removed from the autoclave. The product was diluted with toluene, and the resulting polyvinylbenzocyclobutene was precipitated in methanol. Polyvinylbenzocyclobutene was filtered out, and the solvent was removed. The residue was transferred to a distillation apparatus. The residue was distilled under reduced pressure (127° C., 5 mmHg) to yield 3.0 g (15 mmol, yield 20%) of 5-(4-benzocyclobutenyl)-2-norbornene as a colorless and transparent liquid. ¹H NMR structural identification showed that the present example produced a compound having the formula (2).

¹H NMR Structural Identification

¹H NMR (400 MHz, CDCl₃): δ 7.00-6.22 (m, 3H), 6.15-6.14 (m, 1H), 5.83-5.81 (m, 1H), 3.37-3.32 (m, 1H), 3.11 (s, 4H), 3.04 (m, 1H), 2.92 (m, 1H), 2.19-2.15 (m, 1H), 1.48-1.43 (m, 2H), 1.28-1.24 (m, 1H)

Example 2

Synthesis of Poly(5-(4-benzocyclobutenyl)-2-norbornene) (Formula (3-17), herein after referred to as P1)

A nitrogen-purged pressure-resistant ampule with a stirring bar was charged with 1.0 g (5.1 mmol) of 5-(4-benzocyclobutenyl)-2-norbornene, 10 mg (0.95 mmol) of 1-hexene, and 10 ml of THF. The pressure-resistant ampule was immersed in an oil bath at 70° C. A solution of 1.0 mg of benzylidene(1,3-dimesitylimidazolidine-2-ylidene)(tricyclohexylphosphine)ruthenium dichloride in 3.0 ml of THF was added to the ampule while the solution in the ampule was stirred, thereby initiating polymerization. After two hours, 0.5 ml of ethyl vinyl ether was added to the ampule to terminate the polymerization. The polymerization solution was then cooled, was removed from the ampule, and was diluted with 100 ml of THF. The diluted polymerization solution was poured into 1 L of methanol while vigorous stirring to precipitate P1. P1 was collected by filtration. P1 was dried in a vacuum dryer at 50° C. overnight to yield 0.8 g (yield 80%) of white P1. P1 had molecular weights of Mn $3.4 \times 10^3$ and Mw $6.6 \times 10^3$.

¹H NMR structural identification showed that the present example produced a polymer having the formula (3-17).

¹H NMR Structural Identification

¹H NMR (400 MHz, CDCl₃): δ 7.19-6.52 (3H), 5.78-4.43 (2H), 3.12 (4H), 3.47-0.81 (7H)

Example 3

Synthesis of (5-(4-benzocyclobutenyl)-2-norbornene)-dicyclopentadiene Copolymer (Formula (3-18), herein after referred to as P2)

A nitrogen-purged pressure-resistant ampule with a stirring bar was charged with 1.0 g (5.1 mmol) of 5-(4-benzocyclobutenyl)-2-norbornene, 1.0 g (7.6 mmol) of dicyclopentadiene, 10 mg (0.95 mmol) of 1-hexene, and 20 ml of THF. The pressure-resistant ampule was immersed in an oil bath at 70° C. A solution of 1.0 mg ($1.1 \times 10^{-3}$ mmol) of benzylidene(1, 3-dimesitylimidazolidine-2-ylidene)(tricyclohexylphosphine)ruthenium dichloride in 3.0 ml of THF was added to the ampule while the solution in the ampule was stirred, thereby initiating polymerization. After two hours, 0.5 ml of ethyl vinyl ether was added to the ampule to terminate the polymerization. The polymerization solution was then cooled, was removed from the ampule, and was diluted with 200 ml of THF. The diluted polymerization solution was poured into 1.5 L of methanol while vigorous stirring to precipitate P2. P2 was collected by filtration. P2 was dried in a vacuum dryer at 50° C. overnight to yield 1.8 g (yield 90%) of white P2. P2 had molecular weights of Mn $6.6 \times 10^3$ and Mw $1.4 \times 10^4$. ¹H NMR showed that the copolymer had the ratio of a constitutional repeating unit derived from 5-(4-benzocyclobutenyl)-2-norbornene: a constitutional repeating unit derived from dicyclopentadiene=34% by mole: 6.6% by mole.

49

$^1$H NMR structural identification showed that the present example produced a polymer having the formula (3-18).

$^1$H NMR Structural Identification $^1$H NMR (400 MHz, CDCl$_3$): δ 7.18-6.59 (5-(4-benzocyclobutenyl)-2-norbornene-originated 3H), 5.75-4.59 (5-(4-benzocyclobutenyl)-2-norbornene-originated 2H, dicyclopentadiene-originated 4H), 3.11 (5-(4-benzocyclobutenyl)-2-norbornene-originated 4H), 3.40-0.80 (5-(4-benzocyclobutenyl)-2-norbornene-originated 7H, dicyclopentadiene-originated 6H)

Example 4

Synthesis of Hydrogenated Product of Poly(5-(4-benzocyclobutenyl)-2-norbornene) (Formula (3-19), herein after referred to as P3)

A 100-ml autoclave with an agitator was charge with 4.0 g of P2 prepared in Example 1 and 50 ml of toluene and was then tightly closed. The autoclave was purged with nitrogen several times. A 10-ml recovery flask was charged with 10 mg (1.2×10$^{-2}$ mmol) of benzylidene(1,3-dimesitylimidazolidine-2-ylidene)(tricyclohexylphosphine)ruthenium dichloride, was purged with nitrogen, and was then charged with 3 ml of toluene and 80 mg (1.1 mmol) of ethyl vinyl ether. The solution was stirred at room temperature for 10 minutes. The solution in the flask was pneumatically transported into the autoclave. The autoclave was then purged with hydrogen several times. A hydrogenation reaction was then performed at a hydrogen pressure of 4.5 MPa at a temperature of 150° C. for 6 hours. The reaction solution was cooled, was transferred into a beaker, and was diluted with 350 ml of toluene. The diluted reaction solution was poured into 2 L of methanol while vigorous stirring to precipitate P3. P3 was collected by filtration. The hydrogenated polymer P3 was dried in a vacuum dryer at 50° C. overnight to yield 3.9 g (yield 98%) of white P3. P3 had molecular weights of Mn 4.2×10$^3$ and Mw 8.9×10$^3$. $^1$H NMR showed the disappearance of a 5.78-4.43 ppm peak assigned to the double bond of the main chain of P1 and the retention of a peak around 7.0 ppm assigned to the aromatic ring, indicating hydrogenation of only the double bond of the main chain (hydrogenation percentage of 99.9% or more) and the retention of the benzocyclobutene structure. $^1$H NMR structural identification showed that the present example produced a polymer having the formula (3-19).

$^1$H NMR Structural Identification $^1$H NMR (400 MHz, CDCl$_3$): δ 7.20-6.63 (3H), 3.12 (4H), 2.78-0.35 (11H)

Example 5

Synthesis of Cross-Linked Compound of P1 (Formula (4-1))

200 mg of P1 prepared in Example 2 was charged into a cylindrical metal mold (diameter 10 mm×height 1.2 mm) and was cross-linked at a pressure of 20 MPa at 280° C. for one hour. IR spectroscopy showed the presence of a cross-linked structure. The cross-linked compound had no Tg observed and a linear expansion coefficient of 31 ppm/° C. The cross-linked compound was prepared without using a cross-linker or a cross-linking aid. The cross-linked compound had no air bubble when visually inspected.

50

Example 6

Synthesis of Cross-Linked Compound of P2 (Formula (4-2))

The procedures of Example 5 were performed except that P1 was replaced with P2. IR spectroscopy showed the presence of a cross-linked structure. The cross-linked compound had no Tg observed and a linear expansion coefficient of 53 ppm/° C. The cross-linked compound was prepared without using a cross-linker or a cross-linking aid. The cross-linked compound had no air bubble when visually inspected.

Example 7

Synthesis of Cross-Linked Compound of P3 (Formula (4-3))

The procedures of Example 5 were performed except that P1 was replaced with P3. IR spectroscopy showed the presence of a cross-linked structure. The cross-linked compound was prepared without using a cross-linker or a cross-linking aid. The cross-linked compound had no air bubble when visually inspected. The cross-linked compound had no Tg observed and a linear expansion coefficient of 45 ppm/° C.

Comparative Example 1

The procedures of Example 5 were performed except that the cross-linking temperature was 160° C. IR spectroscopy showed the absence of a cross-linked structure. The formed product had a Tg of 95° C. and a linear expansion coefficient of 77 ppm/° C.

Comparative Example 2

The procedures of Example 6 were performed except that the cross-linking temperature was 160° C. IR spectroscopy showed the absence of a cross-linked structure. The formed product had a Tg of 117° C. and a linear expansion coefficient of 79 ppm/° C.

Comparative Example 3

The procedures of Example 7 were performed except that the cross-linking temperature was 160° C. IR spectroscopy showed the absence of a cross-linked structure. The formed product had a Tg of 70° C. and a linear expansion coefficient of 77 ppm/° C.

Comparative Example 4

The procedures of Example 5 were performed except that P1 was ZEONEX E48R manufactured by Zeon Corp. IR spectroscopy showed the absence of a cross-linked structure. The formed product had a Tg of 135° C. and a linear expansion coefficient of 72 ppm/° C.

Table 1 shows the results of Examples 5 to 7 and Comparative Examples 1 to 3.

TABLE 1

| | Polymer | Forming temperature (° C.) | Detection of cross-linked structure | Tg (° C.) | Linear expansion coefficient (ppm/° C.) |
|---|---|---|---|---|---|
| Example 5 | P1 | 280 | Yes | Not detected | 31 |
| Example 6 | P2 | 280 | Yes | Not detected | 53 |
| Example 7 | P3 | 280 | Yes | Not detected | 45 |
| Comparative example 1 | P1 | 160 | No | 93 | 77 |
| Comparative example 2 | P2 | 160 | No | 116 | 79 |
| Comparative example 3 | P3 | 160 | No | 68 | 77 |
| Comparative example 4 | E48R | 280 | No | 135 | 72 |

Thus, the cross-linked compounds according to the present examples had a small linear expansion coefficient of 60 ppm/° C. or less. The non-crosslinked compounds according to the comparative examples had a large linear expansion coefficient of more than 60 ppm/° C.

The embodiments and examples show that a cross-linked compound of a polymer produced by the polymerization of a compound according to the present invention has a small linear expansion coefficient.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-166969, filed Jul. 29, 2011, which is hereby incorporated by reference herein in its entirety.

The invention claimed is:

1. A compound having the following general formula (I):

$$A\text{-}Z\text{—}B\phi \quad (I)$$

wherein A has the following formula (a), Bφ has the following formula (b1) or (b2), and Z denotes a direct bond (z1) or has one of the formulae (z2) to (z12):

[Chem. 2]

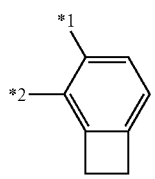

(a)

wherein *1 and *2 denote a bonding arm, one of *1 and *2 is bonded to Z of the formula (I), and the other of *1 and *2 not bonded to Z of the formula (I) is bonded to a hydrogen atom,

[Chem. 3]

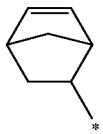

(b1)

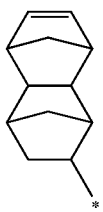

(b2)

wherein * denotes a bonding arm and is bonded to Z of the formula (I), and

[Chem. 4]

[Chem. 4]

(z2)

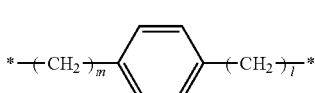

(z3)

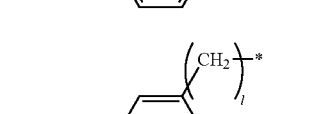

(z4)

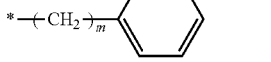

(z5)

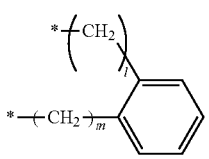

(z6)

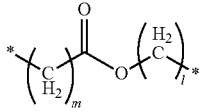

(z7)

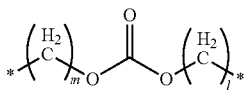

(z8)

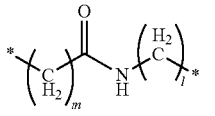

(z9)

-continued

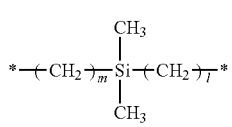  (z10)

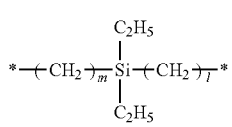  (z11)

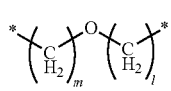  (z12)

wherein two *'s in each of the formulae (z2) to (z12) denote a bonding arm and are bonded to A or Bφ of the formula (I), and n, m, and l independently denote an integer of 0 to 5.

2. A compound having the following general formula (II):

Cφ-Y-D     (II)

wherein Cφ has the following formula (c), D has one of the following formulae (d1) and (d2), and Y is a direct bond (y1) or has one of the formulae (y2) to (y12):

[Chem. 5]

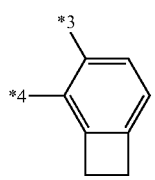  (c)

wherein *3 and *4 denote a bonding arm, one of *3 and *4 is bonded to Y of the formula (II), and the other of *3 and *4 not bonded to Y of the formula (II) is bonded to a hydrogen atom,

[Chem. 6]

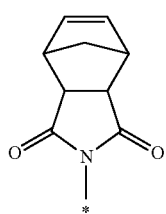  (d1)

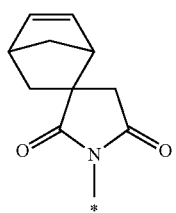  (d2)

wherein * denotes a bonding arm and is bonded to Y of the formula (II), and

[Chem. 7]

*—(CH$_2$)$_n$—*     (y2)

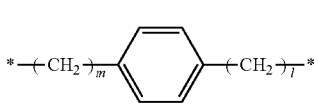  (y3)

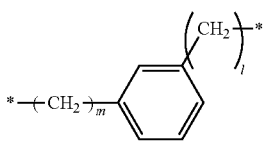  (y4)

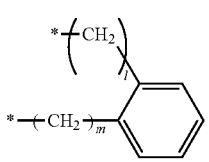  (y5)

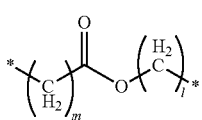  (y6)

  (y7)

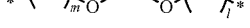  (y8)

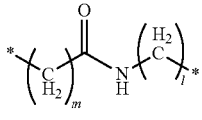  (y9)

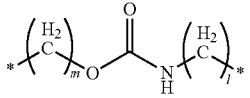  (y10)

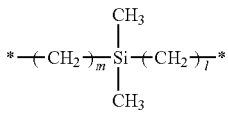  (y11)

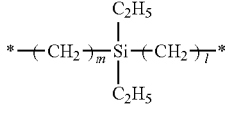  (y12)

wherein two *'s in each of the formulae (y2) to (y12) denote a bonding arm and are bonded to Cφ or D of the formula (II), and n, m, and l independently denote an integer of 0 to 5.

3. A polymer having a constitutional repeating unit represented by one of the formulae (e1) to (e3):

[Chem. 8]

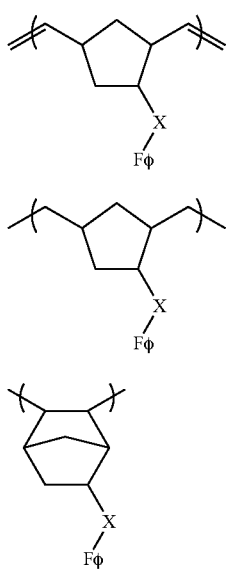
(e1)
(e2)
(e3)

wherein Fφ has the following formula (f), and X is a direct bond (x1) or has one of the formulae (x2) to (x12):

[Chem. 9]

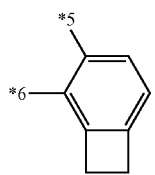
(f)

wherein *5 and *6 denote a bonding arm, one of *5 and *6 is bonded to X of the formulae (e1) to (e3), and the other of *5 and *6 not bonded to X of the formulae (e1) to (e3) is bonded to a hydrogen atom, and

[Chem. 10]

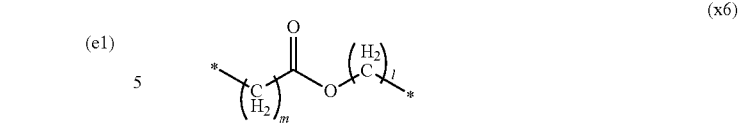
(x2)
(x3)
(x4)
(x5)
(x6)
(x7)
(x8)
(x9)
(x10)
(x11)
(x12)

wherein two *'s in each of the formulae (x2) to (x12) denote a bonding arm and are bonded to a carbon atom of an alicyclic structure or Fφ of the formulae (e1) to (e3), and n, m, and l independently denote an integer of 0 to 5.

4. A polymer having a constitutional repeating unit represented by one of the formulae (g1) to (g3):

[Chem. 11]

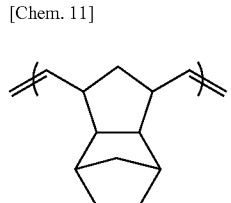
(g1)

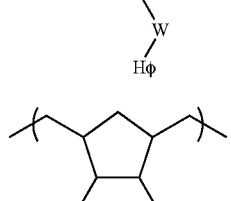
(g2)

(g3)

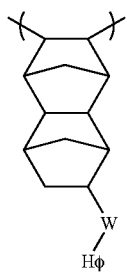

wherein Hφ has the following formula (h), and W is a direct bond (w1) or has one of the formulae (w2) to (w12):

[Chem. 12]

(h)

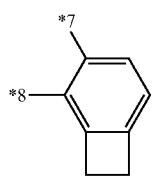

wherein *7 and *8 denote a bonding arm, one of *7 and *8 is bonded to W of the formulae (g1) to (g3), and the other of *7 and *8 not bonded to W of the formulae (g1) to (g3) is bonded to a hydrogen atom, and

[Chem. 13]

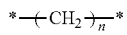 (w2)

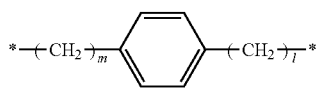 (w3)

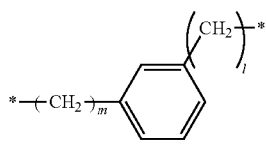 (w4)

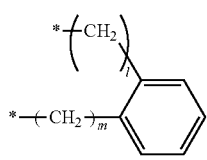 (w5)

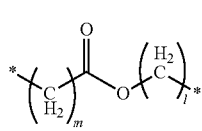 (w6)

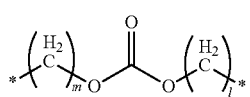 (w7)

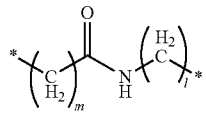 (w8)

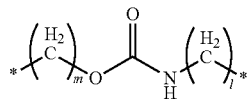 (w9)

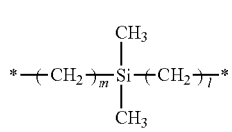 (w10)

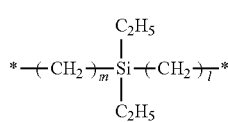 (w11)

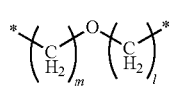 (w12)

wherein two *'s in each of the formulae (w2) to (w12) denote a bonding arm and are bonded to a carbon atom of an alicyclic structure or Hφ of the formulae (g1) to (g3), and n, m, and l independently denote an integer of 0 to 5.

5. A polymer having a constitutional repeating unit represented by one of the formulae (i1) to (i3):

[Chem. 14]

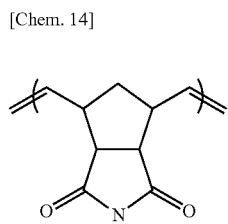 (i1)

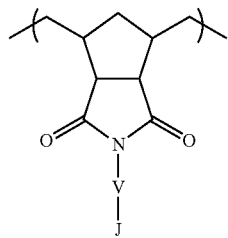 (i2)

(i3)

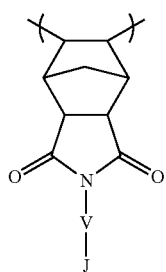

wherein J has the following formula (j), and V is a direct bond (v1) or has one of the formulae (v2) to (v12):

[Chem. 15]

(j)

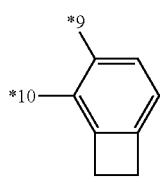

wherein *9 and *10 denote a bonding arm, one of *9 and *10 is bonded to V of the formulae (i1) to (i3), and the other of *9 and *10 not bonded to V of the formulae (i1) to (i3) is bonded to a hydrogen atom, and

[Chem. 16]

(v2)

(v3)

(v4)

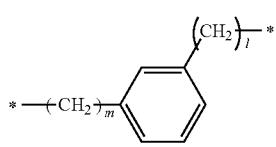

(v5)

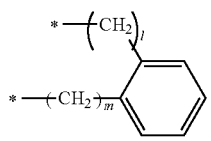

(v6)

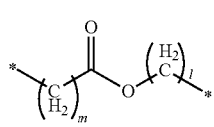

(v7)

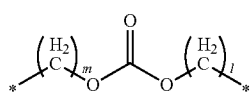

(v8)

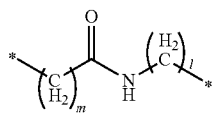

(v9)

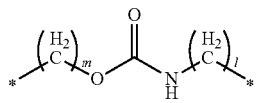

(v10)

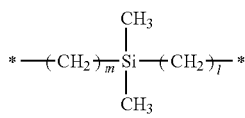

(v11)

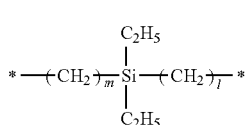

(v12)

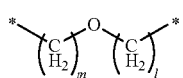

wherein two *'s in each of the formulae (v2) to (v12) denote a bonding arm and are bonded to a nitrogen atom or J of the formulae (i1) to (i3), and n, m, and l independently denote an integer of 0 to 5.

6. A polymer having a constitutional repeating unit represented by one of the formulae (k1) to (k3):

[Chem. 17]

(k1)

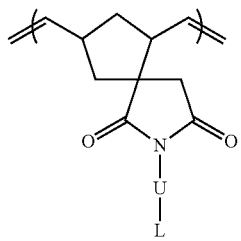

(k2)

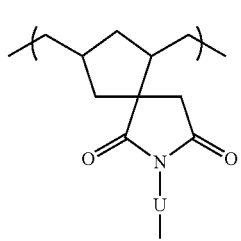

(k3)

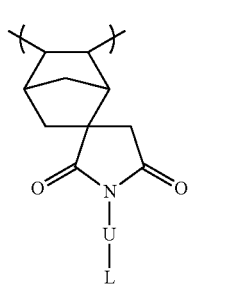

wherein L has the following formula (I), and U is a direct bond (u1) or has one of the formulae (u2) to (u12):

[Chem. 18]

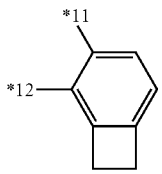

(I)

wherein *11 and *12 denote a bonding arm, one of *11 and *12 is bonded to U of the formulae (k1) to (k3), and the other of *11 and *12 not bonded to U of the formulae (k1) to (k3) is bonded to a hydrogen atom, and

[Chem. 19]

  (u2)

  (u3)

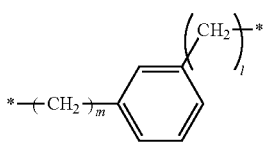  (u4)

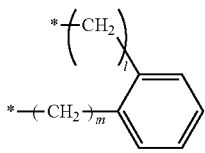  (u5)

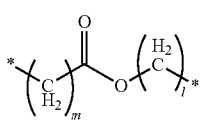  (u6)

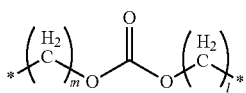  (u7)

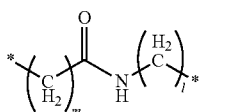  (u8)

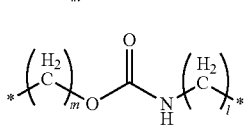  (u9)

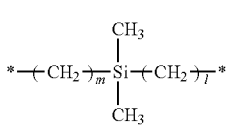  (u10)

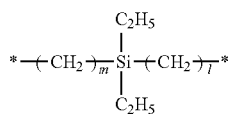  (u11)

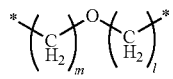  (u12)

wherein two *'s in each of the formulae (u2) to (u12) denote a bonding arm and are bonded to a nitrogen atom or L of the formulae (k1) to (k3), and n, m, and l independently denote an integer of 0 to 5.

7. A cross-linked compound having the general formula (III):

M-R-T-R'-M'    (III)

wherein M and M' are polymers having a constitutional repeating unit represented by one of the formulae (m1) to (m12), and each of R and R' is a direct bond (r1) or has one of the formulae (r2) to (r12), and T has the formula (t):

[Chem. 20]

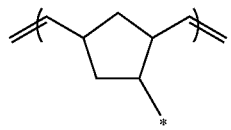  (m1)

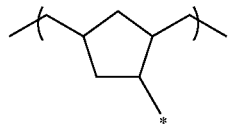  (m2)

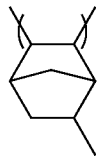  (m3)

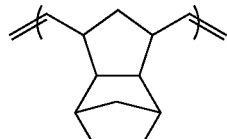  (m4)

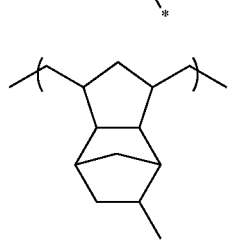  (m5)

-continued
(m6)
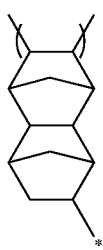
(m7)
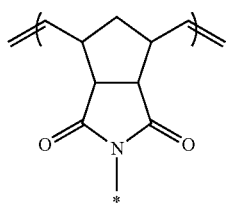
(m8)
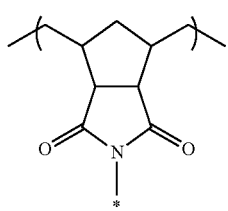
(m9)
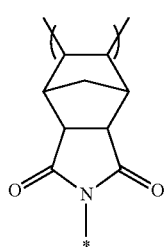
(m10)
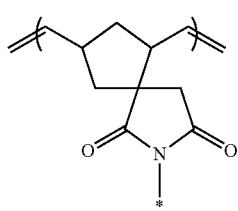
(m11)
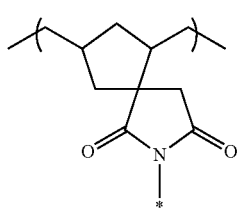
-continued
(m12)
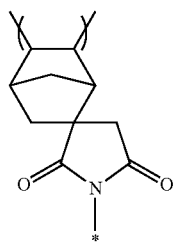
wherein * denotes a bonding arm and is bonded to R or R' of the formula (III),
[Chem. 21]
(r2)
(r3)
(r4)
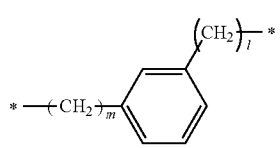
(r5)
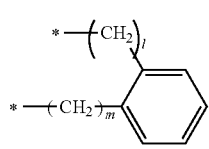
(r6)
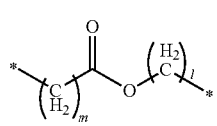
(r7)
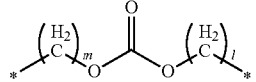
(r8)
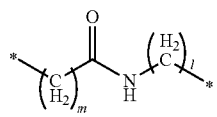
(r9)
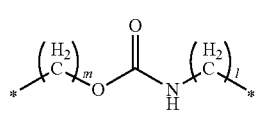
(r10)
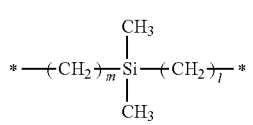
(r11)
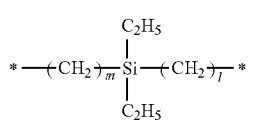

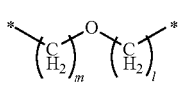
(r12)

wherein two *'s in each of the formulae (r2) to (r12) denote a bonding arm and are bonded to M or M' or T of the formula (III), and n, m, and l independently denote an integer of 0 to 5, and

[Chem 22]

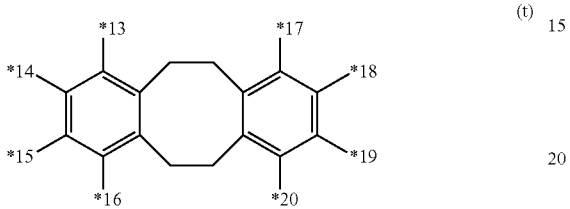
(t)

wherein *13 to *20 denote a bonding arm, one of *13 to *16 and one of *17 to *20 are bonded to M and M' of the formula (III), and the remainder of *13 to *20 not bonded to M or M' of the formula (III) are bonded to a hydrogen atom.

8. An optical element having an organic transparent member, wherein the organic transparent member contains a crosslinked compound according to claim 7.

* * * * *